US012611268B2

(12) United States Patent     (10) Patent No.:    US 12,611,268 B2

Danziger et al.            (45) Date of Patent:     Apr. 28, 2026

(54) BRAKE RELEASE FOR SURGICAL ROBOT

(71) Applicant: Auris Health, Inc., Redwood City, CA (US)

(72) Inventors: Benjamin Danziger, Kenmore, WA (US); Jennifer Bauer, San Francisco, CA (US); Eyal Aklivanh, Belmont, CA (US); Caroline Michelle Gilley, Mountain View, CA (US); Lewis Theodore Cronis, Mendon, MA (US); Rochelle Rea, San Leandro, CA (US)

(73) Assignee: Auris Health, Inc., Santa Clara, CA (US)

( * ) Notice: Subject to any disclaimer, the term of this patent is extended or adjusted under 35 U.S.C. 154(b) by 230 days.

(21) Appl. No.: 18/326,629

(22) Filed: May 31, 2023

(65) Prior Publication Data

US 2024/0398490 A1     Dec. 5, 2024

(51) Int. Cl.
     *A61B 34/30*       (2016.01)
     *A61B 90/00*       (2016.01)
     *A61B 90/50*       (2016.01)

(52) U.S. Cl.
     CPC ............... *A61B 34/30* (2016.02); *A61B 90/06* (2016.02); *A61B 90/08* (2016.02); *A61B 2034/305* (2016.02); *A61B 2090/066* (2016.02)

(58) Field of Classification Search
     CPC .............. A61B 2034/305; A61B 34/30; A61B 2090/508
     See application file for complete search history.

(56) References Cited

U.S. PATENT DOCUMENTS

| | | | |
|---|---|---|---|
| 9,763,741 B2 | 9/2017 | Alvarez et al. | |
| 2015/0345571 A1 | 12/2015 | Yi et al. | |
| 2018/0289445 A1* | 10/2018 | Krinninger | ............ A61B 34/30 |
| 2018/0353246 A1* | 12/2018 | Ishihara | ................ A61B 34/25 |
| 2020/0212763 A1 | 7/2020 | Takata et al. | |
| 2021/0022817 A1 | 1/2021 | Thakkar | |

(Continued)

FOREIGN PATENT DOCUMENTS

| | | | |
|---|---|---|---|
| CN | 108223623 A | 6/2018 | |
| JP | 4277964 B2 * | 6/2009 | ............. A61B 90/11 |
| WO | WO-2022076686 A1 * | 4/2022 | ......... A61B 17/1214 |

OTHER PUBLICATIONS

Frameless Stereotactic Surgery Device JP 4277964 Bw (Year: 2009).*

(Continued)

*Primary Examiner* — Brian T Gedeon

(74) *Attorney, Agent, or Firm* — FBT Gibbons LLP

(57)          ABSTRACT

A medical robotic system can include a secondary brake release to allow a user to more easily move the arms of the robotic system when the system is in a power-off or fault state. The robotic system can include a joint and a brake mechanism that can limit motion of the joint. The brake mechanism can include a braking material, a first electromagnetic assembly, and a user-commanded release mechanism. The first electromagnetic assembly can disengage the braking material from an engaged configuration to a disengaged configuration. Further, the user-commanded release device can disengage the braking material from the engaged configuration to the disengaged configuration independent of the first electromagnetic assembly.

20 Claims, 34 Drawing Sheets

(56)         References Cited

U.S. PATENT DOCUMENTS

| | | |
|---|---|---|
| 2021/0028727 A1 | 1/2021 | Tan et al. |
| 2021/0085410 A1* | 3/2021 | Hassan .................. A61B 34/32 |
| 2023/0086127 A1* | 3/2023 | Ishikawa ................. H02J 1/086 |
| | | 307/18 |

OTHER PUBLICATIONS

International Search Report and Written Opinion dated Sep. 11, 2024, for International Application No. PCT/IB2024/055338, 7 pages.

* cited by examiner

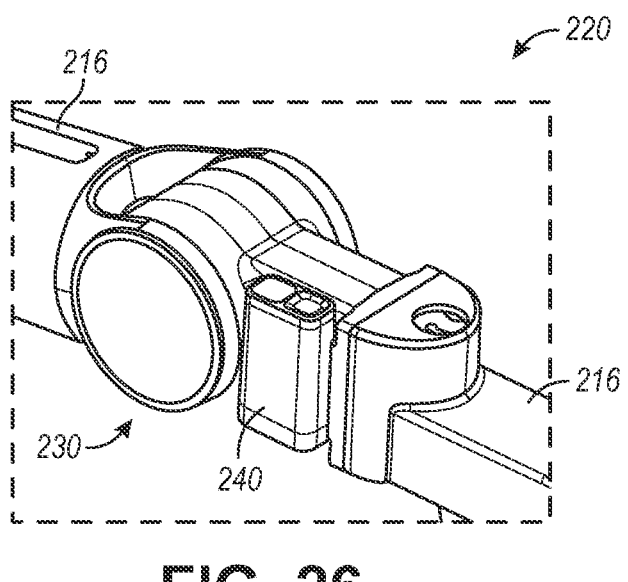
FIG. 26
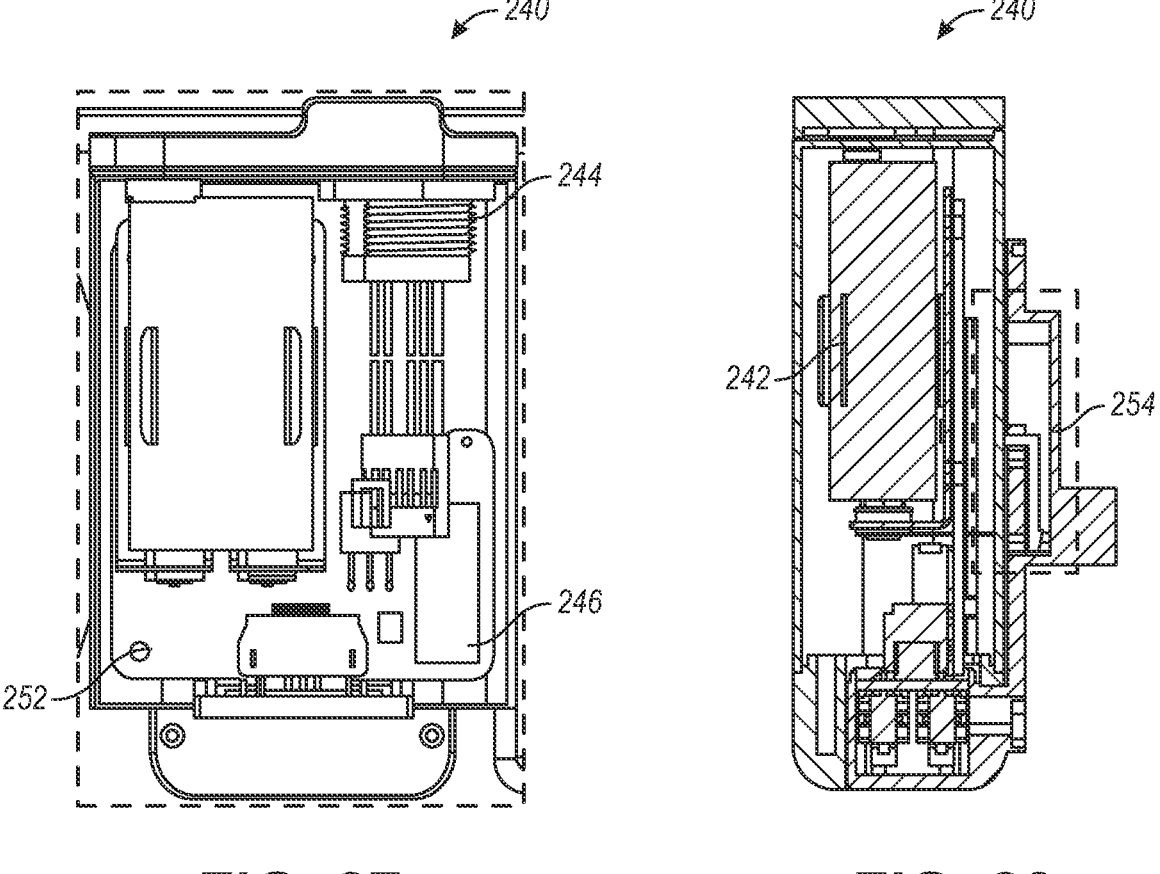
FIG. 27          FIG. 28

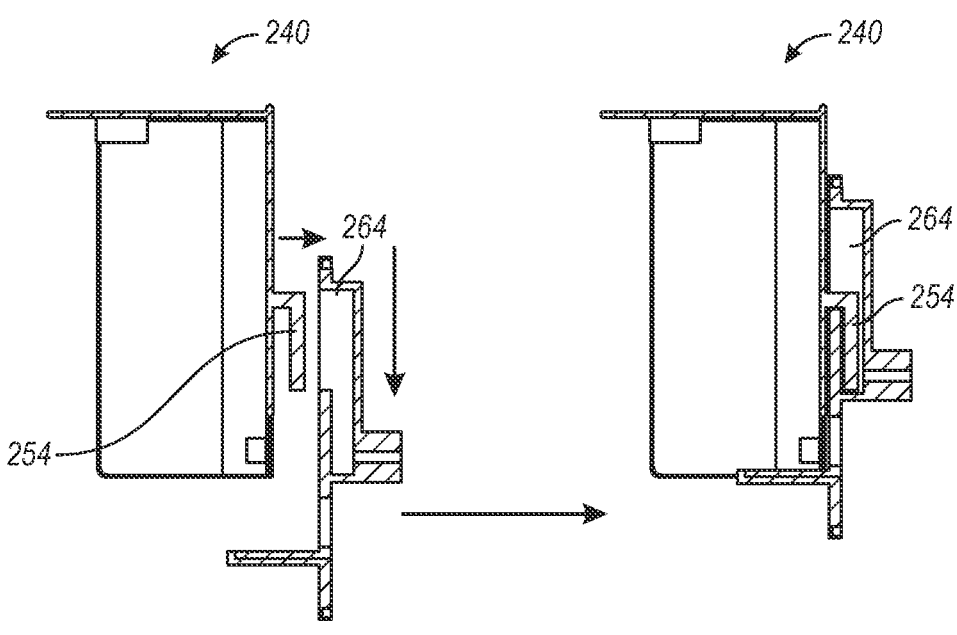
FIG. 31A          FIG. 31B
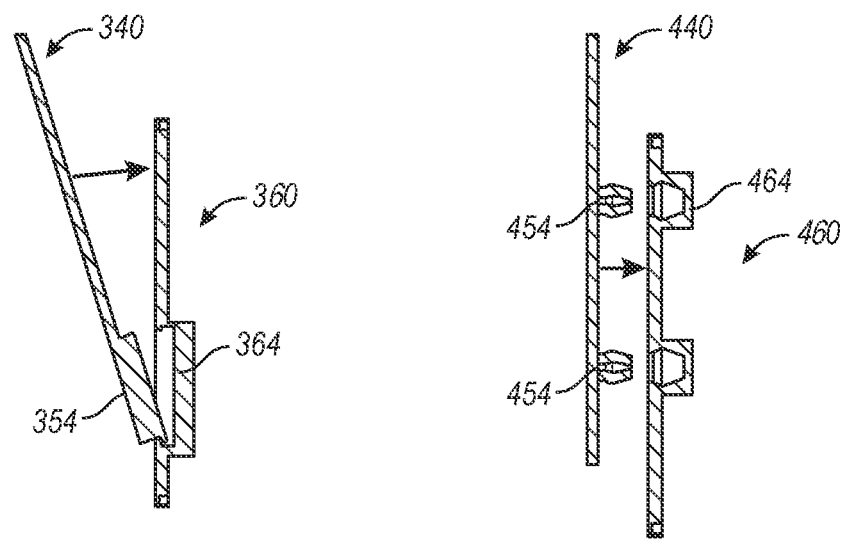
FIG. 32          FIG. 33

BRAKE RELEASE FOR SURGICAL ROBOT

TECHNICAL FIELD

Systems and methods disclosed herein related to robotic systems, and more particularly to brake releases for robotic systems.

BACKGROUND

Minimally invasive procedures allow for access to a targeted site within a patient with minimal trauma to the patient. A medical robotic system can provide a mechanism through which one or more robotic arms are used to perform a surgical operation. For example, laparoscopic surgery can allow for surgical access to a patient's cavity through a small incision on the patient's abdomen.

The robotic arms of the robotic system can be coupled to one or more tools, such as a cannula or other devices, that will be used to perform the surgical operation on a patient. Each arm can include one or more joints to position the arms in space. In turn, the joints can be driven by motors and/or transmissions that facilitate the movement of the arms and any tools carried thereby through space, relative to the patient.

The arms of the robotic system, once in a power-off or fault state, will generally be held in place via a braking mechanism (e.g., as "power-off brakes"). The braking mechanism can be provided in the joints and links of the arm, thereby inhibiting movement of the arm and prevent access to the patient. The power-off brakes may be activated automatically by a controller or control system of the robotic system, such as upon triggering of a fault (e.g., if a sensor were to break) or upon loss of power to the system.

SUMMARY

In some predicate systems, these power-off brakes may be sufficient to maintain the arm in a given position while permitting the arm to be "back-drivable" by the user. When back-driven by the user, the user would apply a force greater than the force of the power-off brake that is used to maintain a joint or link in a given position. As a result, the user would be able to articulate the arm to a given desired position even when the power-off brakes are activated in the arm. In addition, such robotic systems can include a primary brake release, which can be activated by the user and implemented by the controller or control system.

In accordance with some embodiments disclosed herein is the realization that as robotic systems developed by the present Applicant continue to evolve and provide functionality and durability hitherto unavailable, important and unexpected changes to the structure and architecture of the robotic system were discovered and found to provide surprisingly important and advantageous results in facilitating the effective and simple operations of the robotic system. Further, in accordance with some embodiments disclosed herein is the realization that the controller or control system of the robotic system may be rendered inoperable or otherwise unavailable to initiate the primary brake release. As such, the present disclosure addresses these and other challenges.

For example, due to the unique architecture of embodiments of robotic systems developed by the present Applicant, unique and innovative architecture has made it possible for components of the system to include joints and brakes that are far sturdier than predicate counterparts. These joints and brakes can be designed to support very heavy weight and cannot simply be overcome by manual user-applied force. In general, many of these joints cannot be back-driven because they support heavy loads.

Accordingly, in addition to a primary brake release that may be available to release the power-off brake system, as discussed above, some embodiments disclosed herein provide a robotic system that incorporates a secondary brake release that can allow the user to release the power-off brake to permit the user to, for example, more easily manipulate the position of a robotic arm while the system is in a power-off or faulted state.

Advantageously, some embodiments of a secondary brake release can allow a user to perform one of a variety of operations or procedures, including accessing a patient on the bed of the system, without impacting the connection between the power-off brake and the motor driver. Moreover, the integrity and function of the system can be more securely protected and maintained while providing flexibility to the user in operating the system. Such secondary brake release mechanisms can provide a solution to the above-noted challenges and have not been disclosed or implemented in predicate systems given that such systems did not implement or otherwise contemplate the unique improvements of Applicant's new technology until the discovery and development of embodiments of the secondary brake release devices.

In accordance with some embodiments, the secondary brake release devices can be implemented as an electrical brake release device. In some embodiments, the electrical brake release device can release a brake mechanism that is associated with and/or coupled to a main joint that enables translation of an adjustable bar relative to the table of the system. In addition to or alternatively, some embodiments of the electrical brake release device can be used to release a brake mechanism that is associated with and/or coupled to one or more joints beyond the main joint. In some embodiments, one or more brake release devices can release one or more joints. Further, an electrical brake release mechanism can be incorporated into a single robotic arm, a pair of robotic arms that operate in tandem, and/or combinations thereof.

In some embodiments, the release device can provide an electrical interface between a power supply and can be configured to provide an electrical connection between the power supply and an electromagnetic brake. The electromagnetic brake can be selectively energized by the power supply independent of a control system of the medical robotic system to disengage the electromagnetic brake and permit articulation of a robotic joint. In addition to, or alternatively, the electrical interface can include an inductive loop.

In some embodiments, the power supply can include a battery, a capacitor, and/or any other suitable power source, including grid power. Optionally, the release device can include a switch to control the electrical connection between the power supply and the electromagnetic brake. Further, in some embodiments, the release device can include a charging circuit.

In some embodiments, the release device includes a thermal protection circuit and/or timing circuit, which can be configured to reduce a power output of the release device in response to a device temperature exceeding a temperature threshold and/or reduce a power output of the release device in response to a device operation period exceeding an operation period threshold. The thermal protection circuit can include a thermistor, a thermocouple, and/or a thermal fuse.

In some embodiments, the release device is configured to communicate with the control system of the medical robotic system.

Advantageously, these systems can provide an added level of safety to a robot that interacts with humans, by allowing joints to be completely unlocked and repositioned even under complete electrical or software failure of the robot.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 26 illustrates a perspective view of a joint with a brake release device, in accordance with some embodiments.

FIG. 27 is a front elevation view of the brake release device of FIG. 26.

FIG. 28 is a cross-sectional side of the brake release device of FIG. 26.

FIG. 31A illustrates a cross-sectional view of a brake release device and the mounting plate of FIG. 30, in accordance with some embodiments.

FIG. 31B illustrates a cross-sectional view of a brake release device and the mounting plate of FIG. 30, in accordance with some embodiments.

FIG. 32 illustrates a cross-sectional view of a brake release device and a mounting plate, in accordance with some embodiments.

FIG. 33 illustrates a cross-sectional view of a brake release device and a mounting plate, in accordance with some embodiments.

DETAILED DESCRIPTION

1. Overview

Aspects of the present disclosure may be integrated into a robotically enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart

Figure 1:
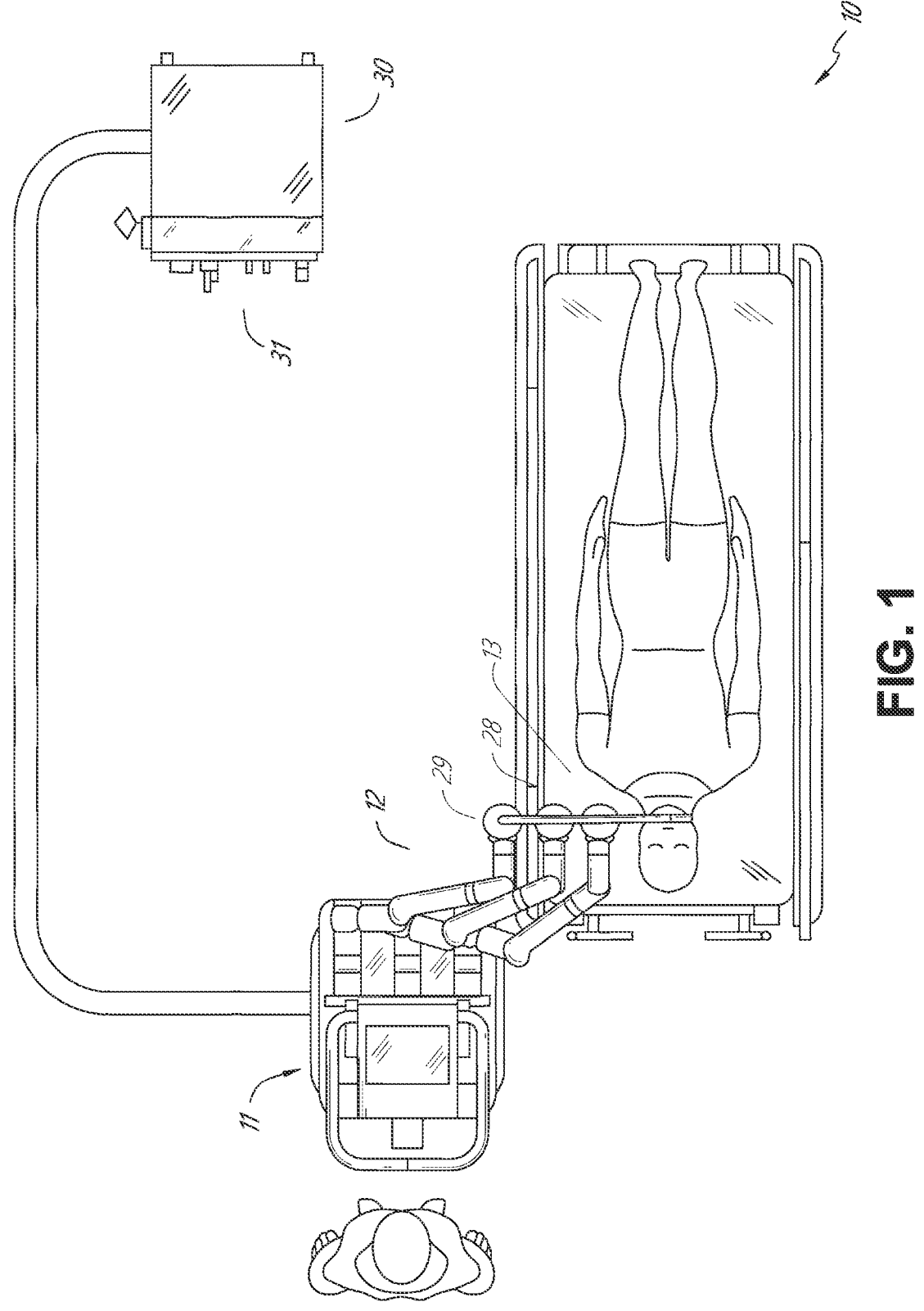
FIG. 1 illustrates an embodiment of a cart-based robotic system arranged for diagnostic and/or therapeutic bronchoscopy procedure(s).
Figure 2:
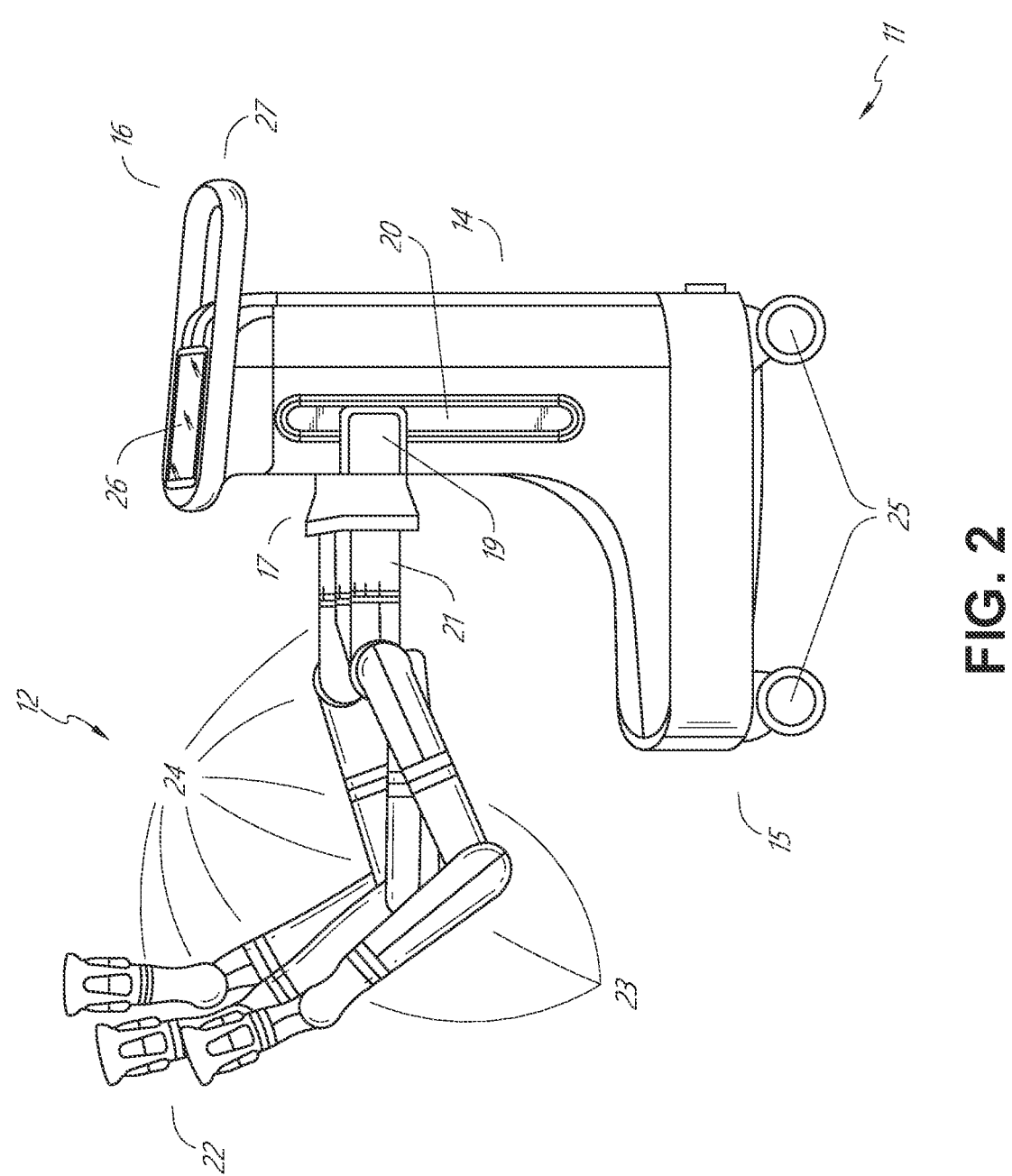
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
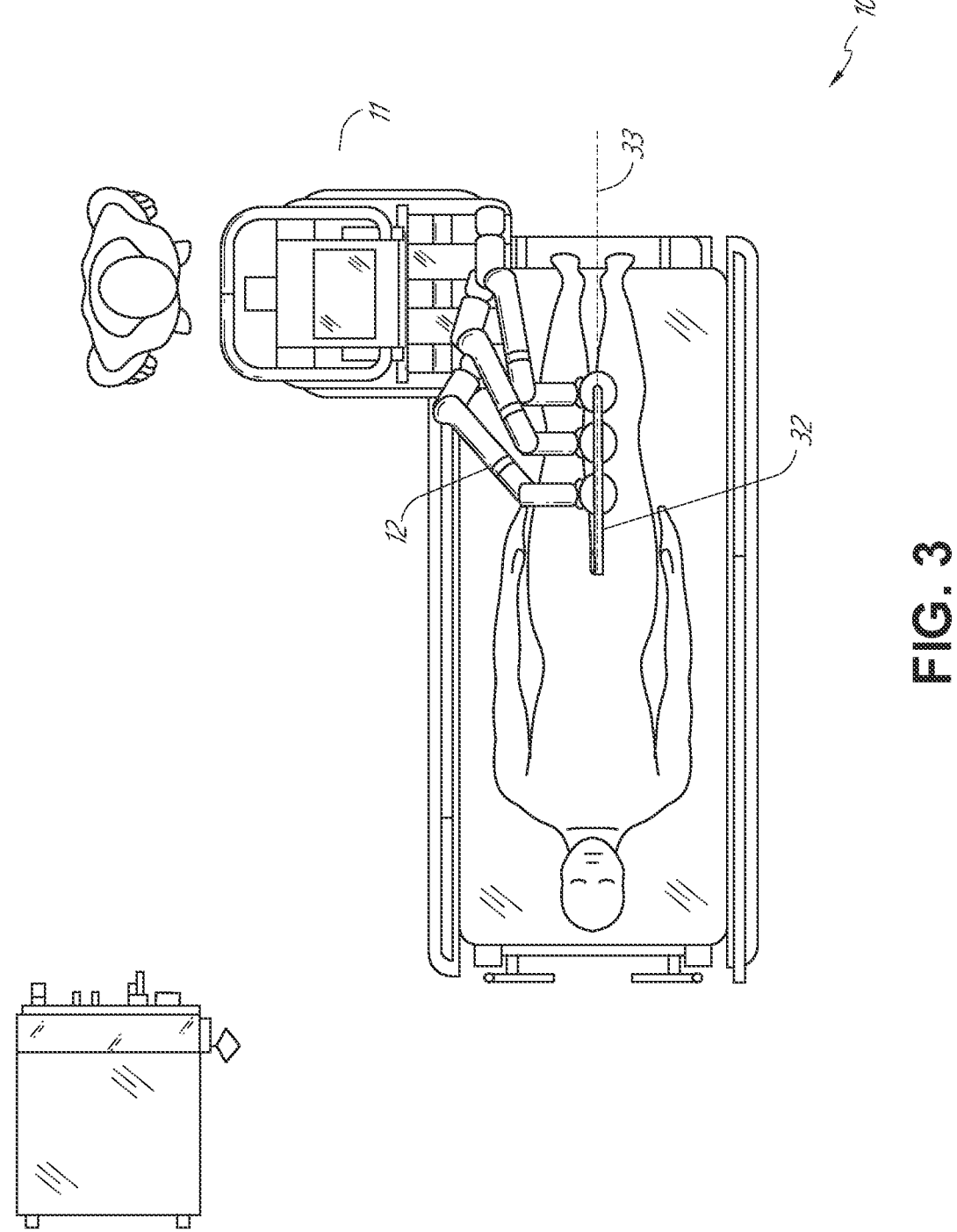
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
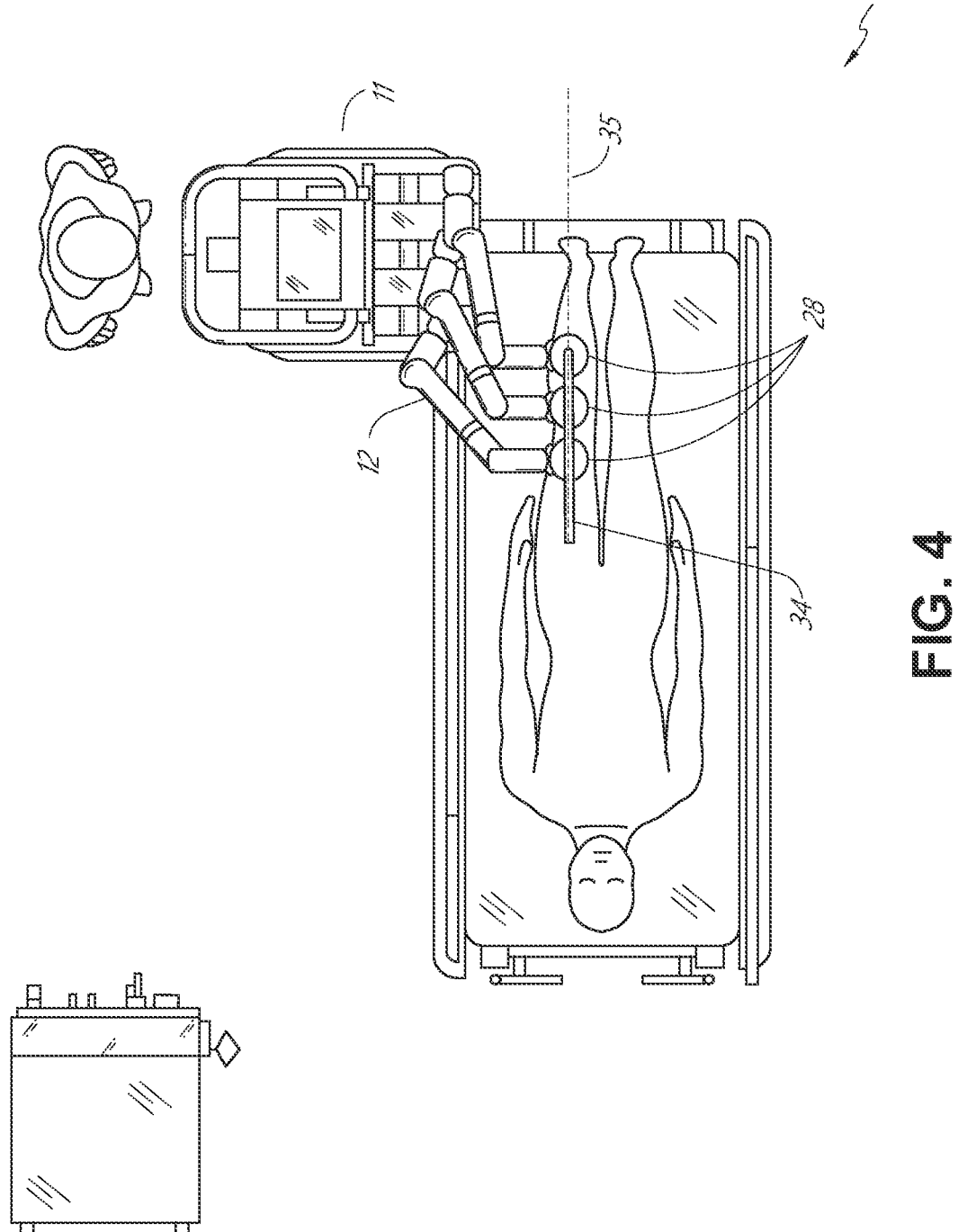
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table

Figure 5:
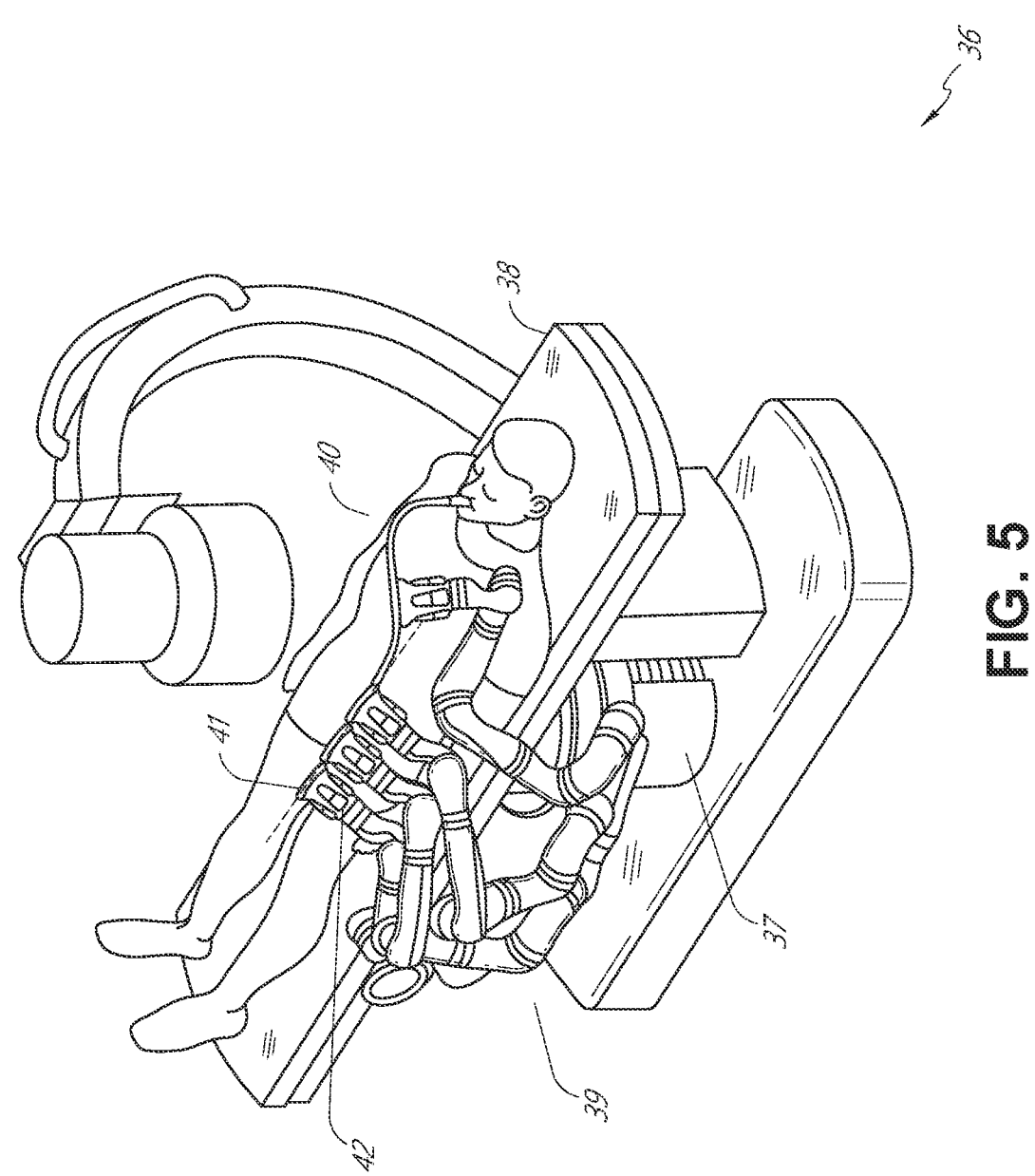
FIG. 5 illustrates an embodiment of a table-based robotic system arranged for a bronchoscopy procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
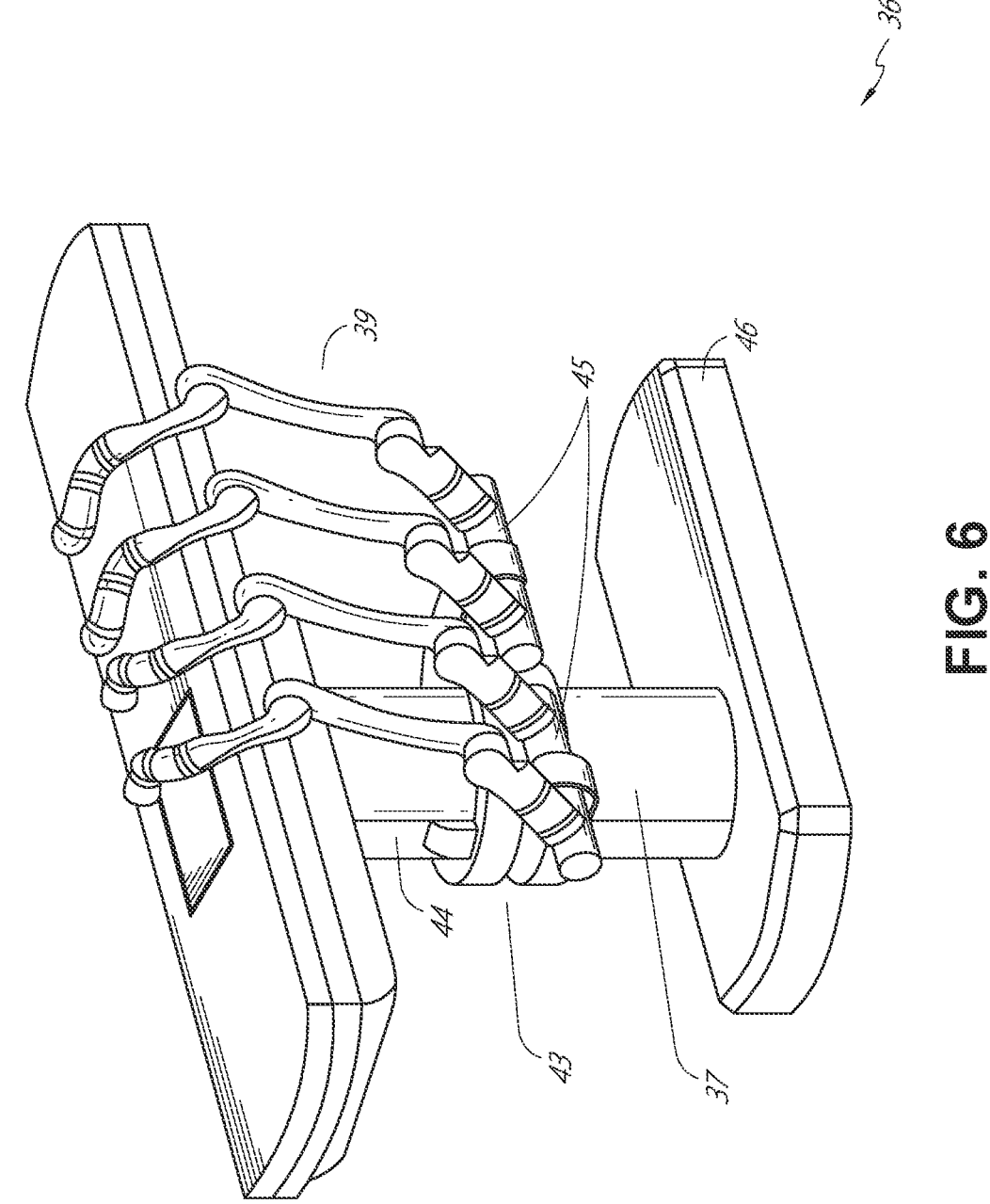
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
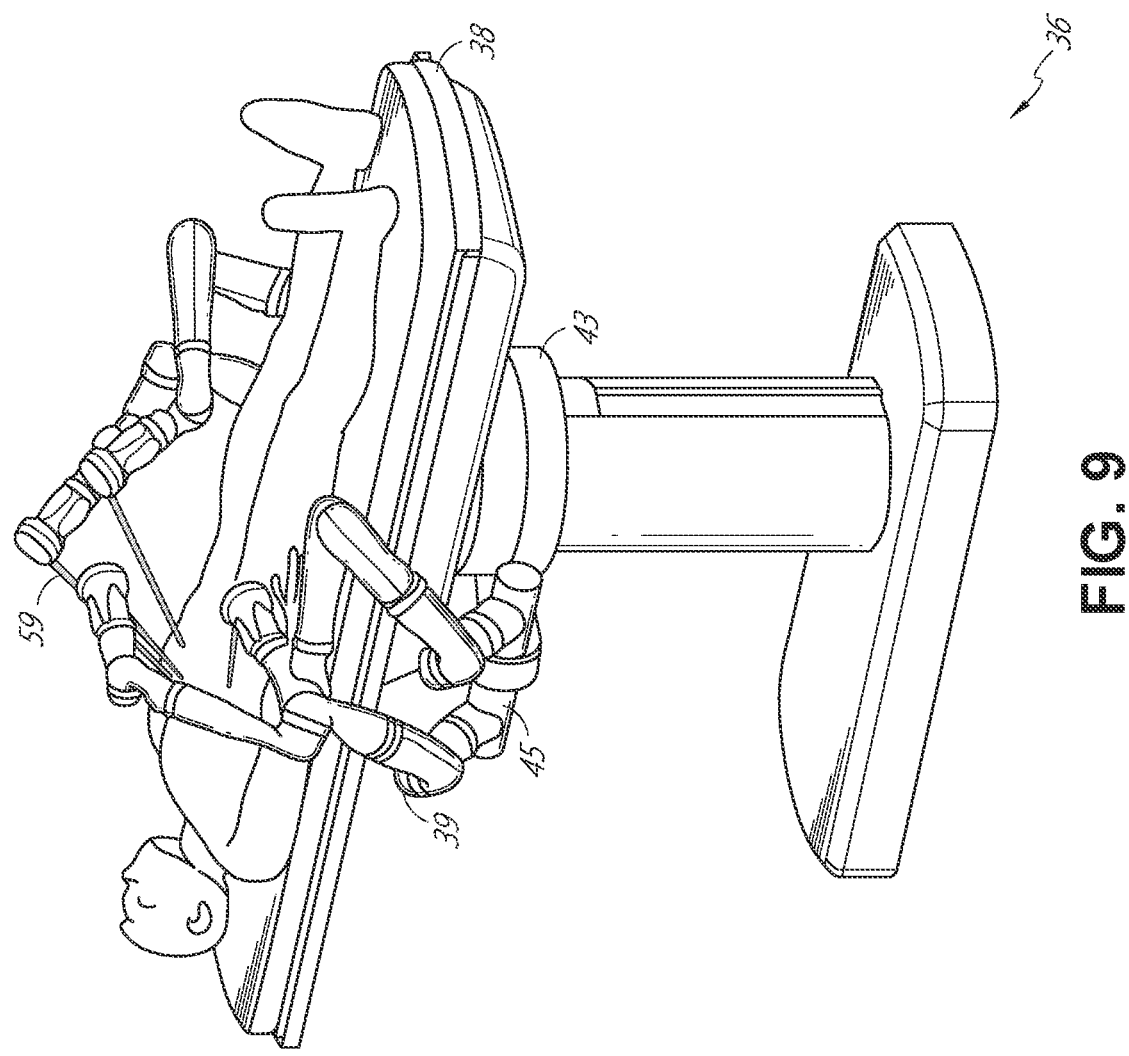
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
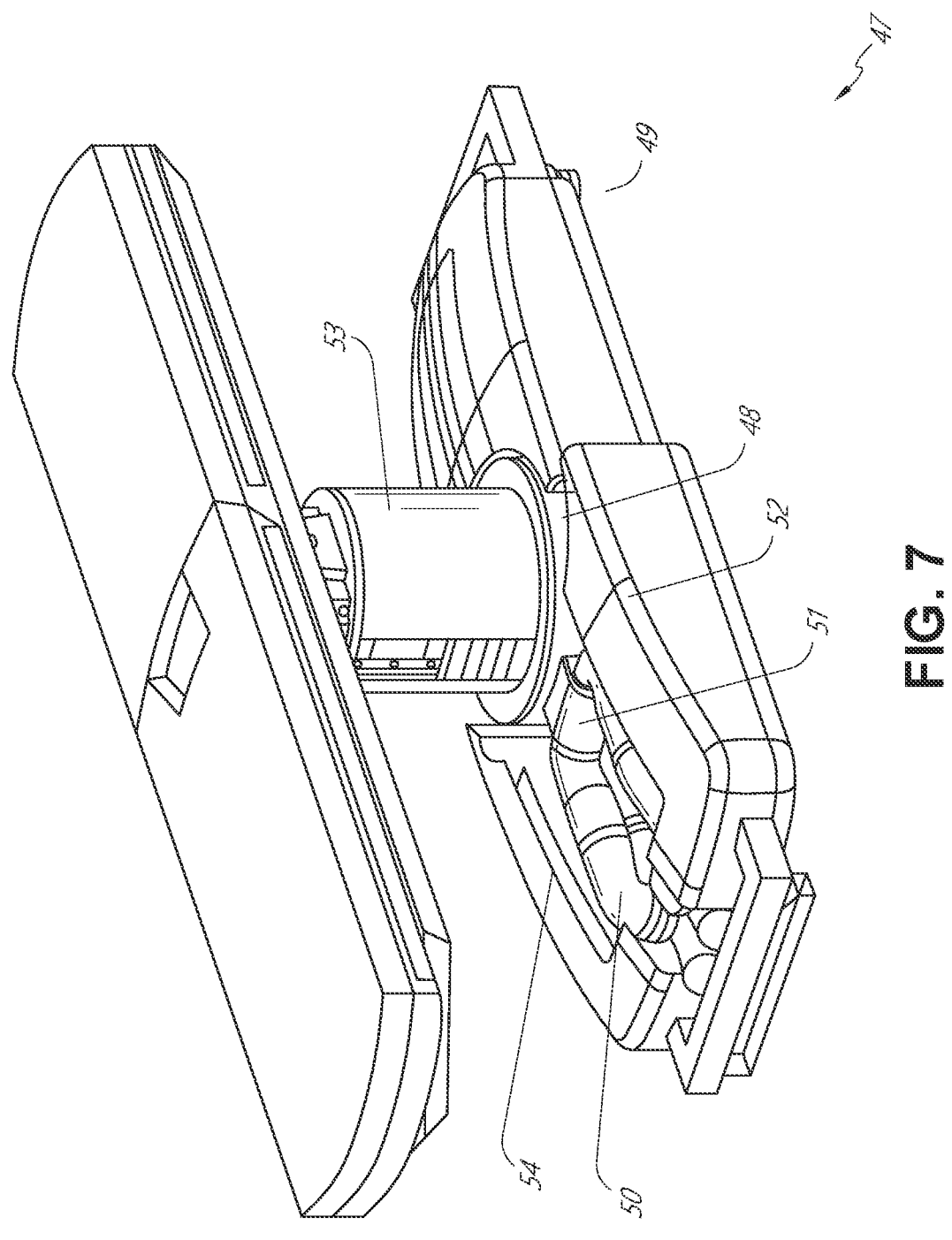
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
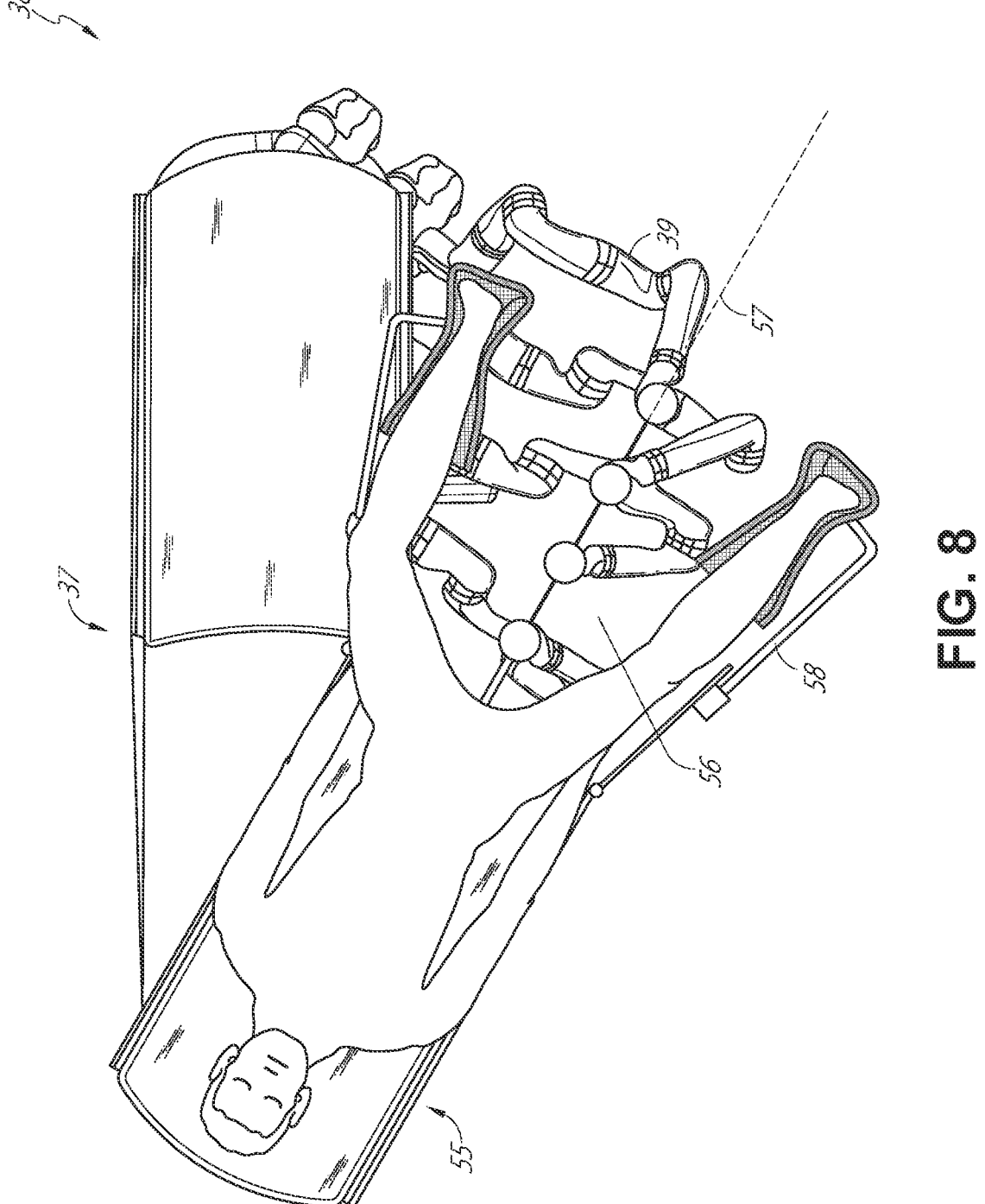
FIG. 8 illustrates an embodiment of a table-based robotic system configured for a ureteroscopy procedure.

FIG. 8 illustrates an embodiment of a robotically enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
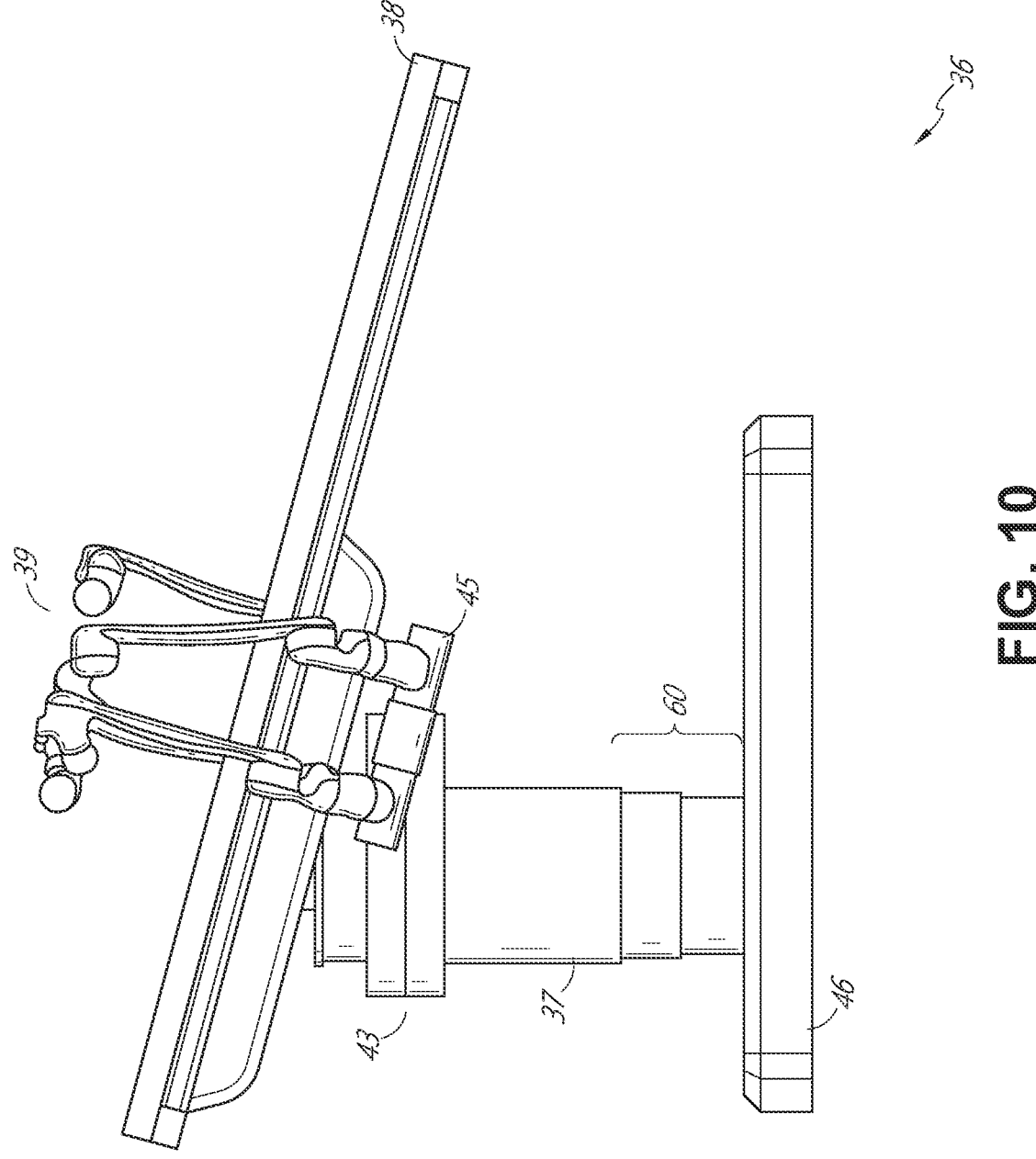
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
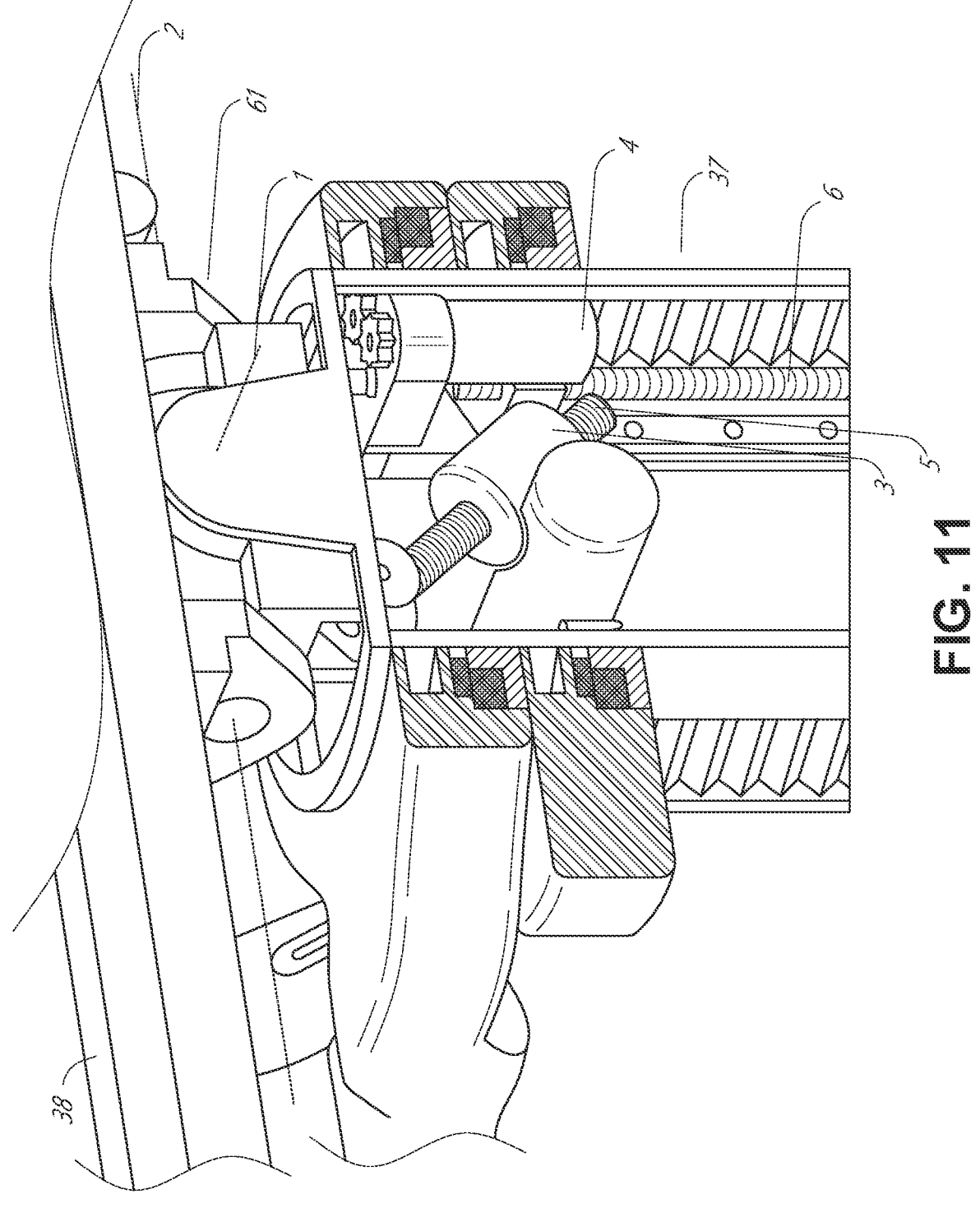
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
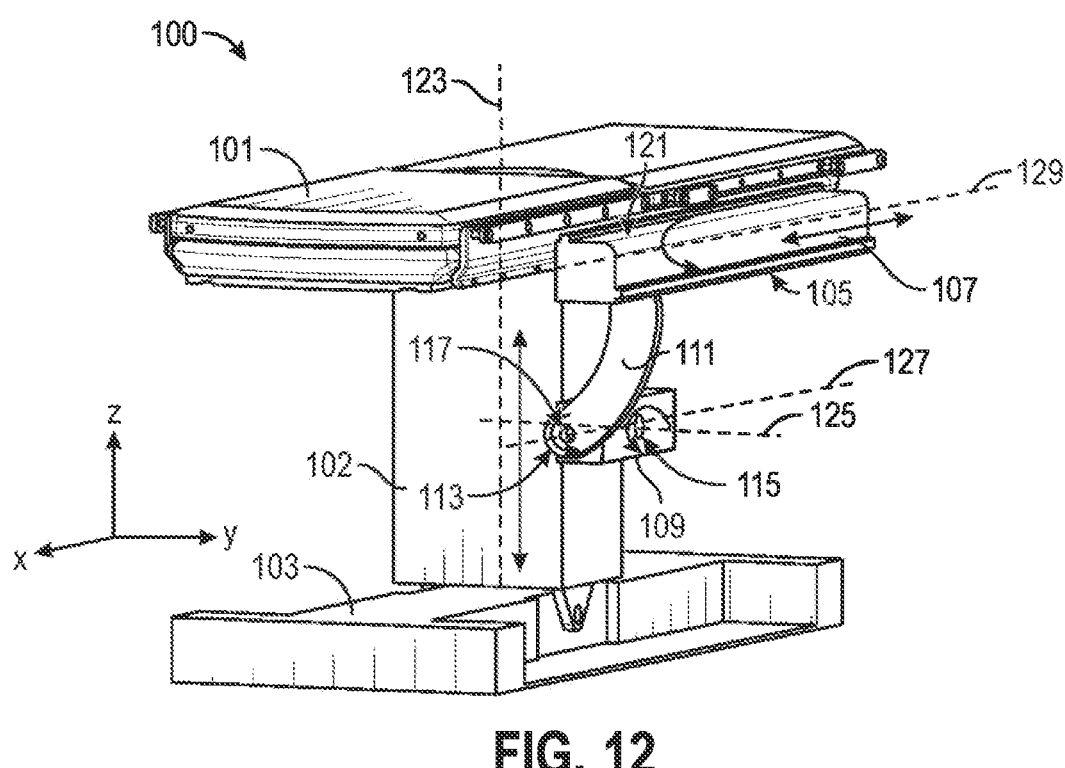
FIG. 12 illustrates an alternative embodiment of a table-based robotic system.
Figure 13:
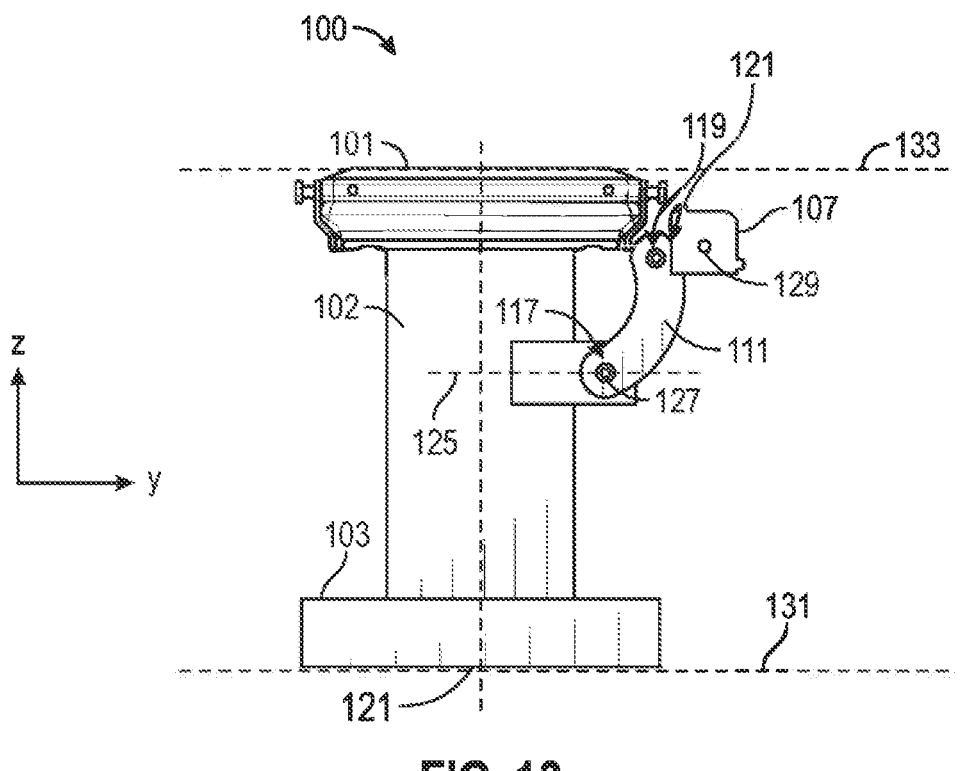
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105.

A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
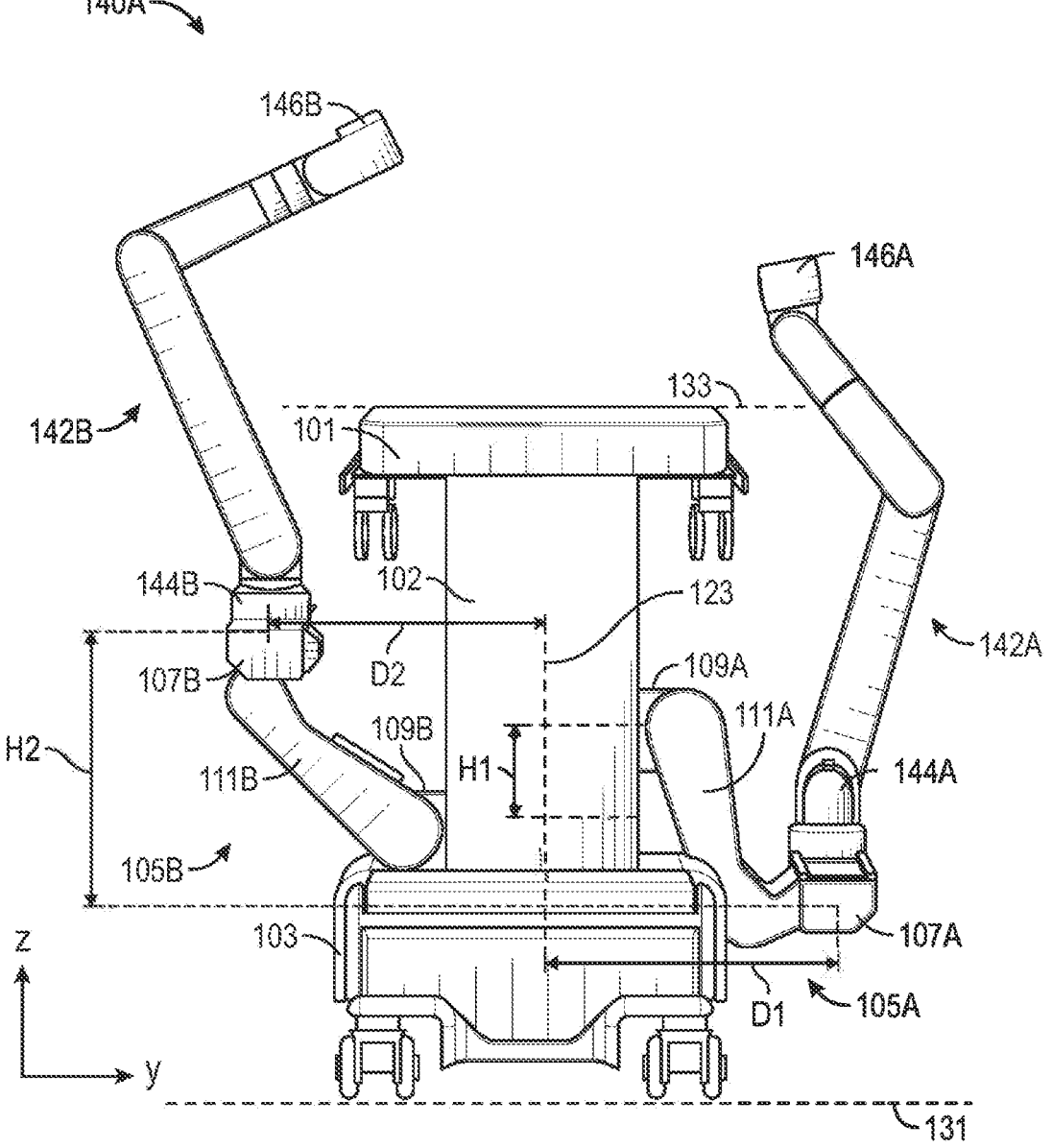
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (one degree of freedom, including insertion), a wrist (three degrees of freedom, including wrist pitch, yaw, and roll), an elbow (one degree of freedom, including elbow pitch), a shoulder (two degrees of freedom, including shoulder pitch and yaw), and base 144A, 144B (one degree of freedom, including translation). In some embodiments, the insertion degree of freedom can be provided by the robotic arm 142A, 142B, while in other embodiments, the instrument itself provides insertion via an instrument-based insertion architecture.

C. Instrument Driver & Interface

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
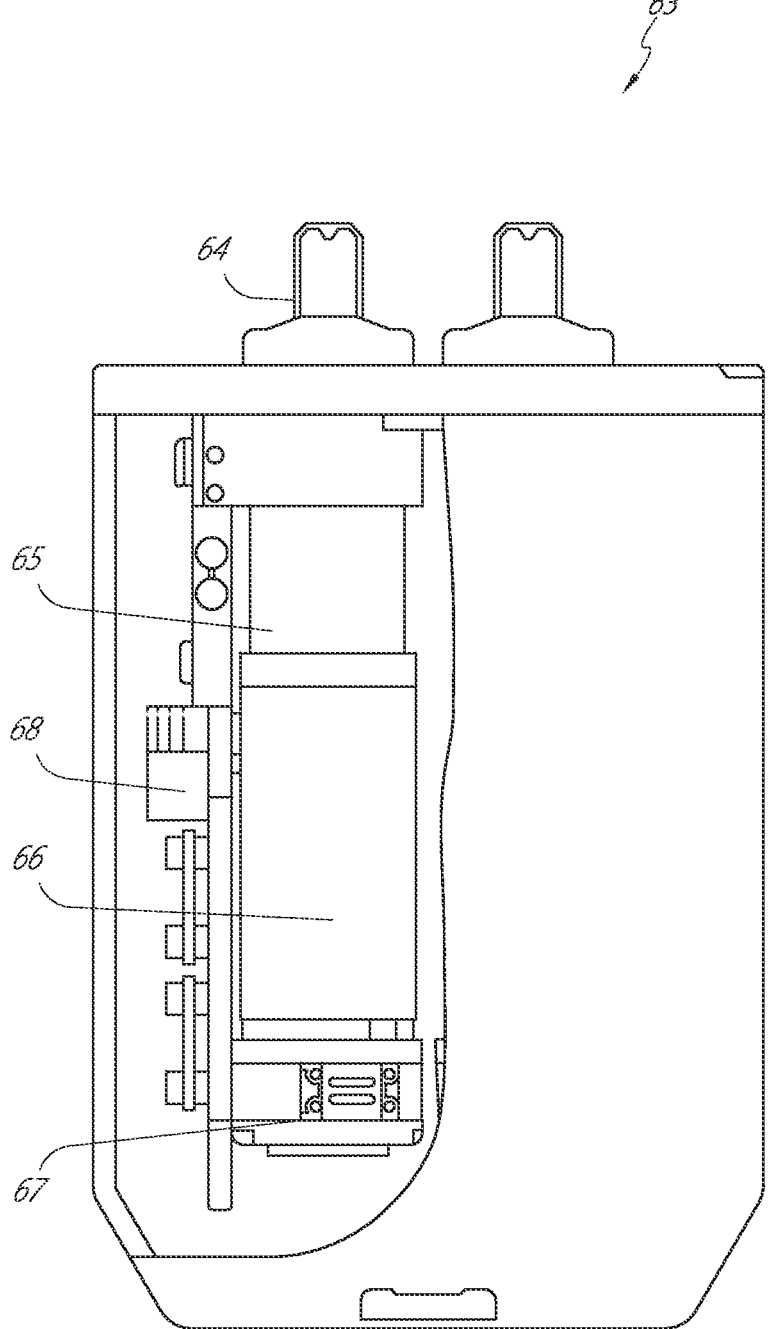
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

Figure 16:
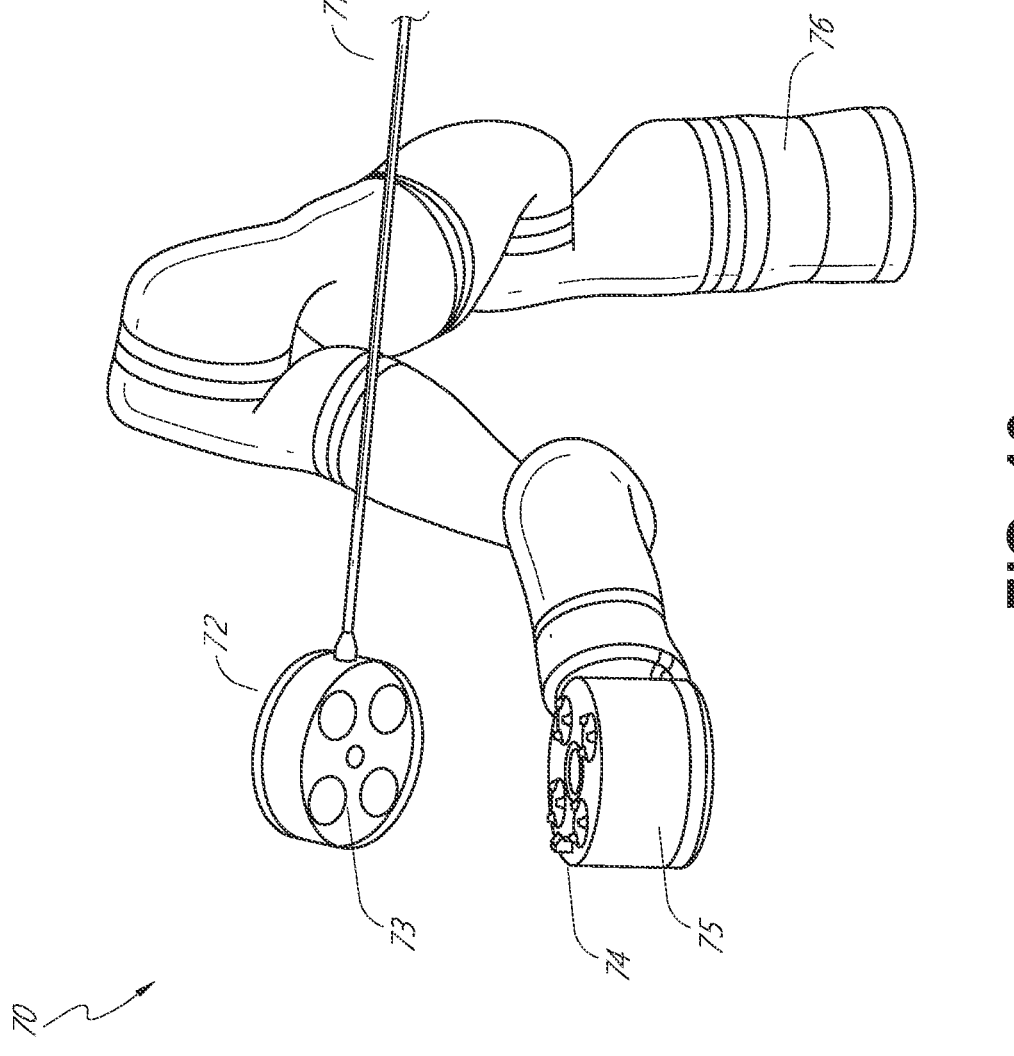
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
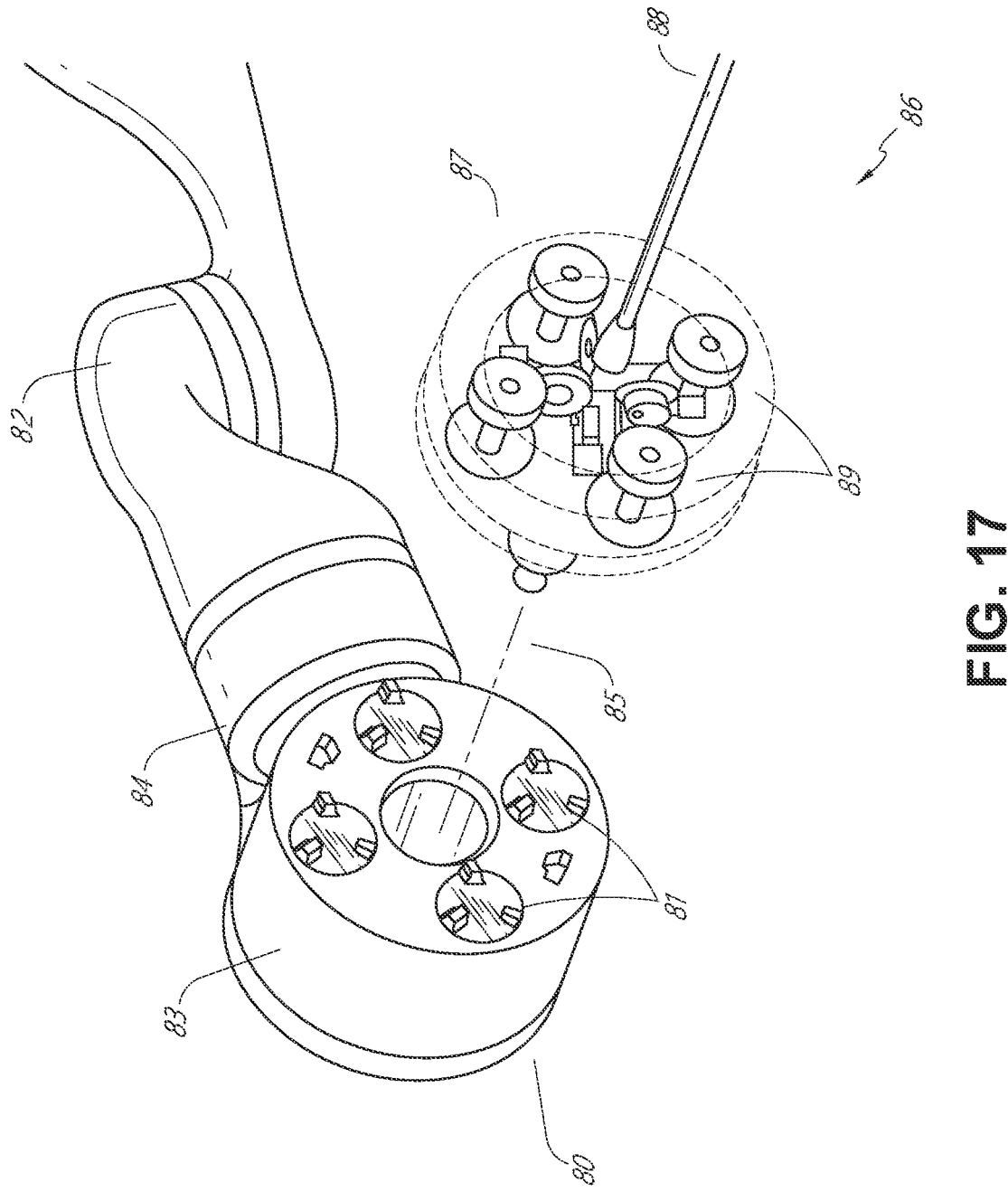
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
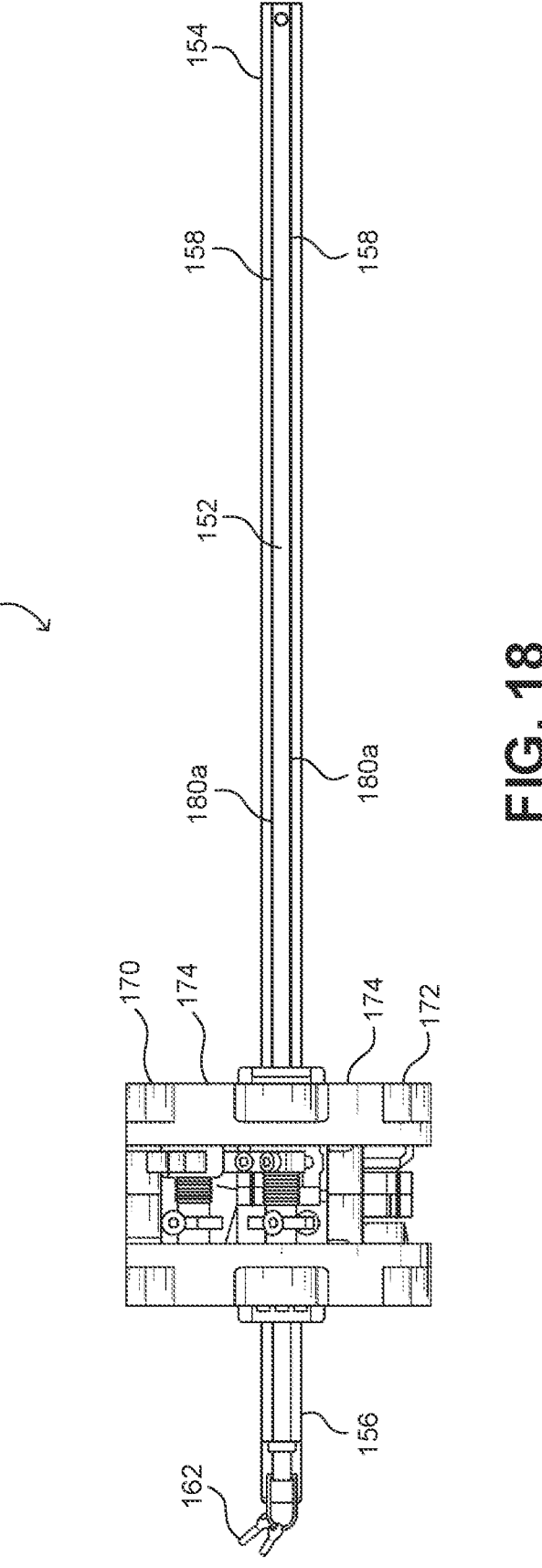
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
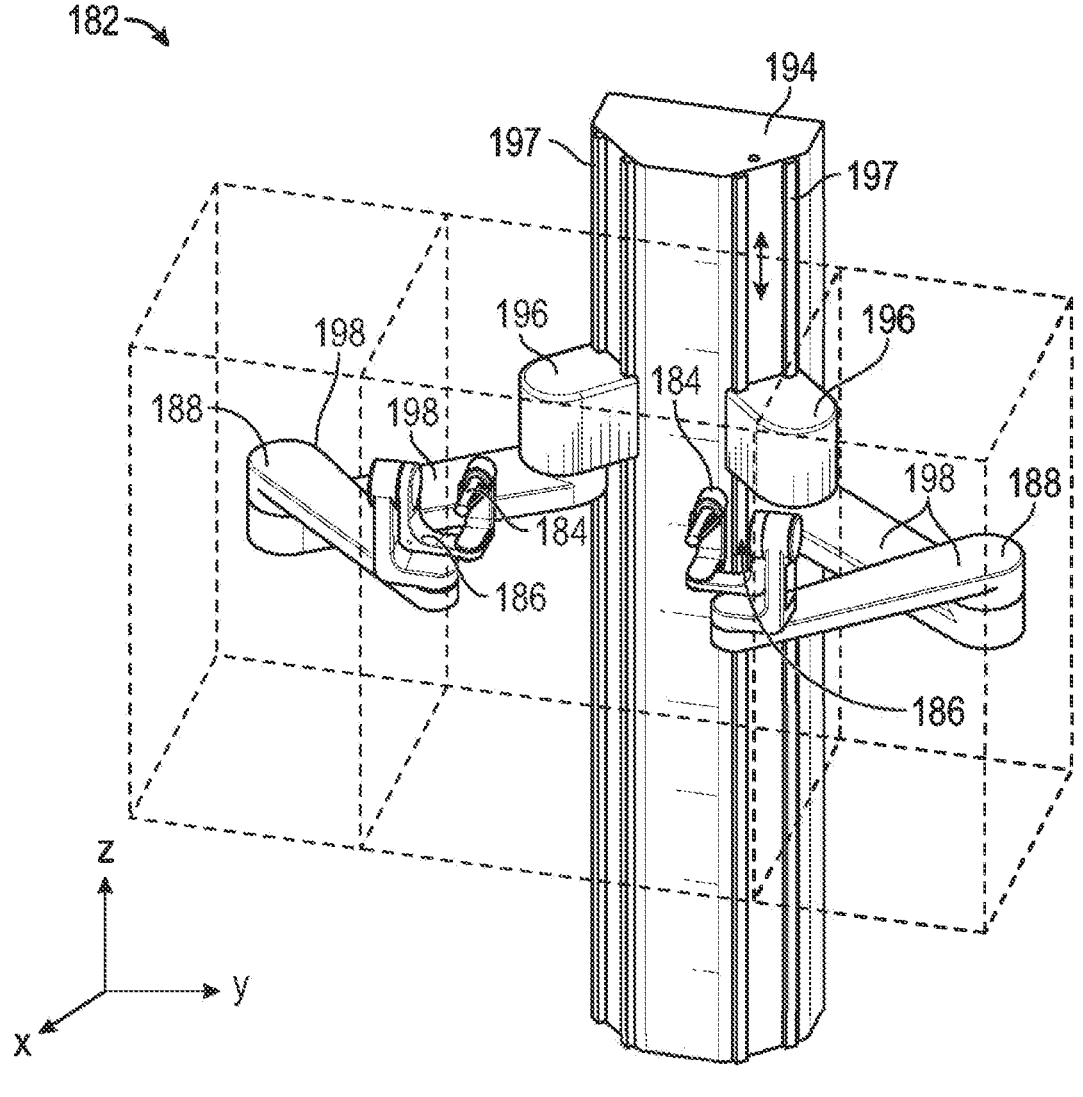
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
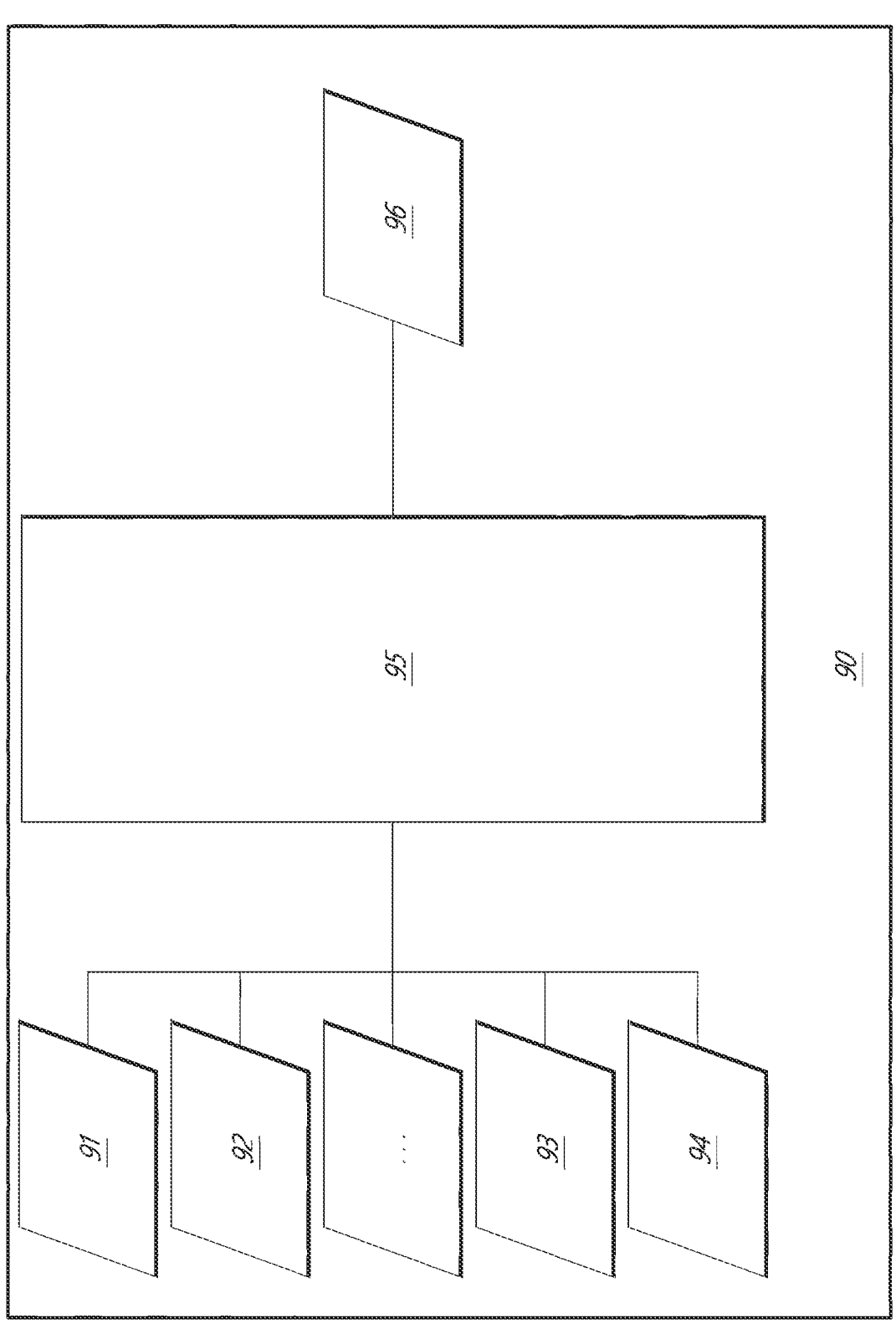
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, issued as U.S. Pat. No. 9,763,741 on Sep. 19, 2017, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Brake Release Devices

In accordance with some embodiments, a robotic system can be configured such that once in a power-off or fault state, the arms can generally be held in place via a braking mechanism (e.g., as "power-off brakes"). The braking mechanism can be located in and around the joints and links of the arm, thereby inhibiting movement of the arm and prevent access to the patient.

The power-off brakes may be activated automatically by a controller or control system of the robotic system, such as upon triggering of a fault (e.g., if a sensor were to break) or upon loss of power to the system. In certain systems, these power-off brakes may be sufficient to maintain the arm in a given position while permitting the arm to be "back-drivable" by the user. When back-driven by the user, the user would apply a force greater than the force of the power-off brake that is used to maintain a joint or link in a given position. As a result, the user would be able to articulate the arm to a given desired position even when the power-off brakes are activated in the arm. In addition, such robotic systems can include a primary brake release, which can be activated by the user and implemented by the controller or control system.

However, in certain robotic systems, including those described above, certain arms may be challenging to back-drive when a power-off brake is applied. The robotic system 200 can comprise a unique architecture in which components thereof include joints and brakes that are far sturdier than predicate counterparts. As noted above, these joints and brakes can be designed to support the very heavy weight of the robotic system's components, such as the table 204, the arms 210, the instrument driver 212, and the instrument 214, and cannot simply be overcome by manual force or otherwise backdriven, at least because they support heavy loads.

Figure 21A:
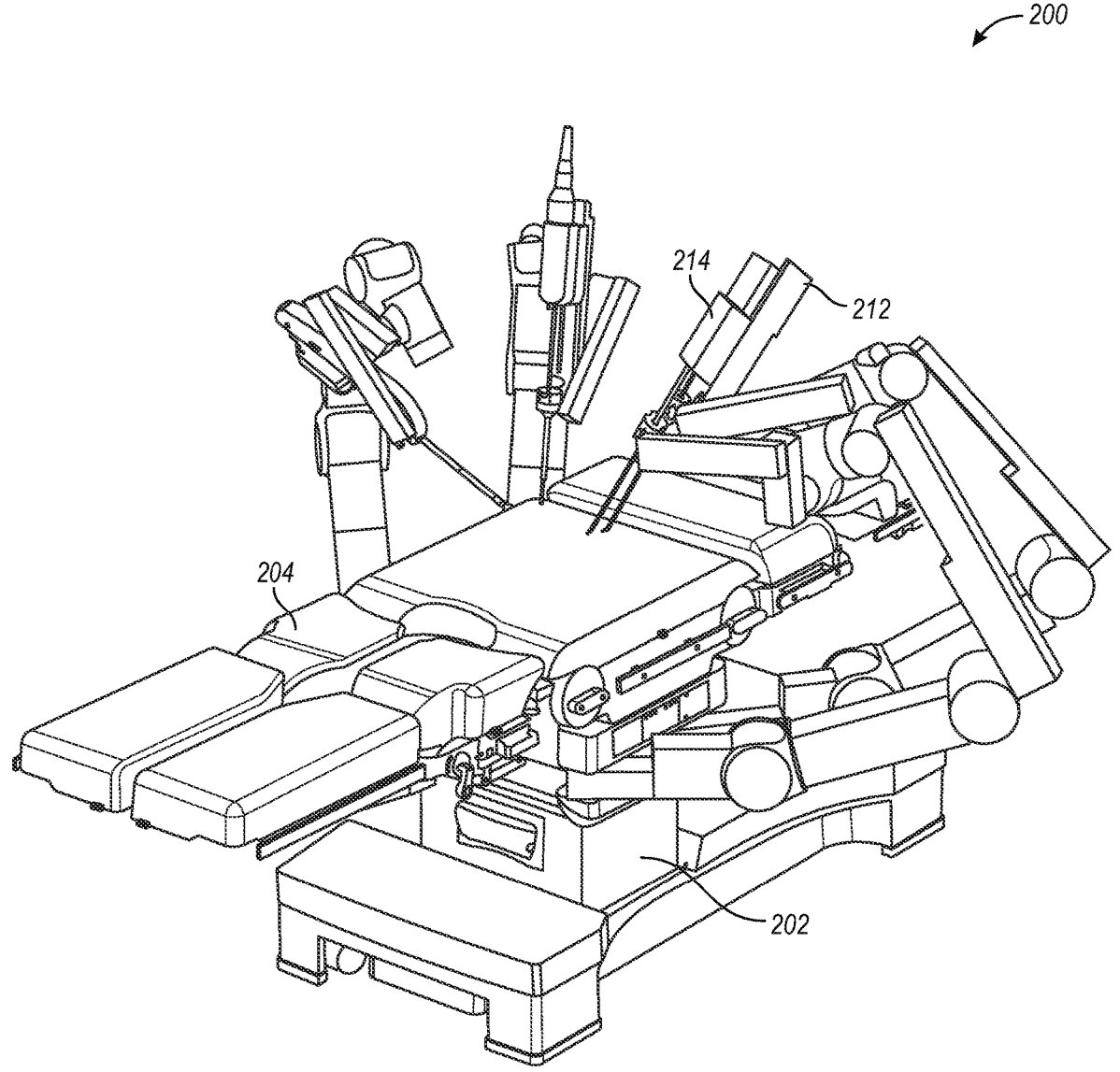
FIG. 21A illustrates a medical robotic system that can utilize one or more brake release mechanisms, in accordance with some embodiments.
Figure 21B:
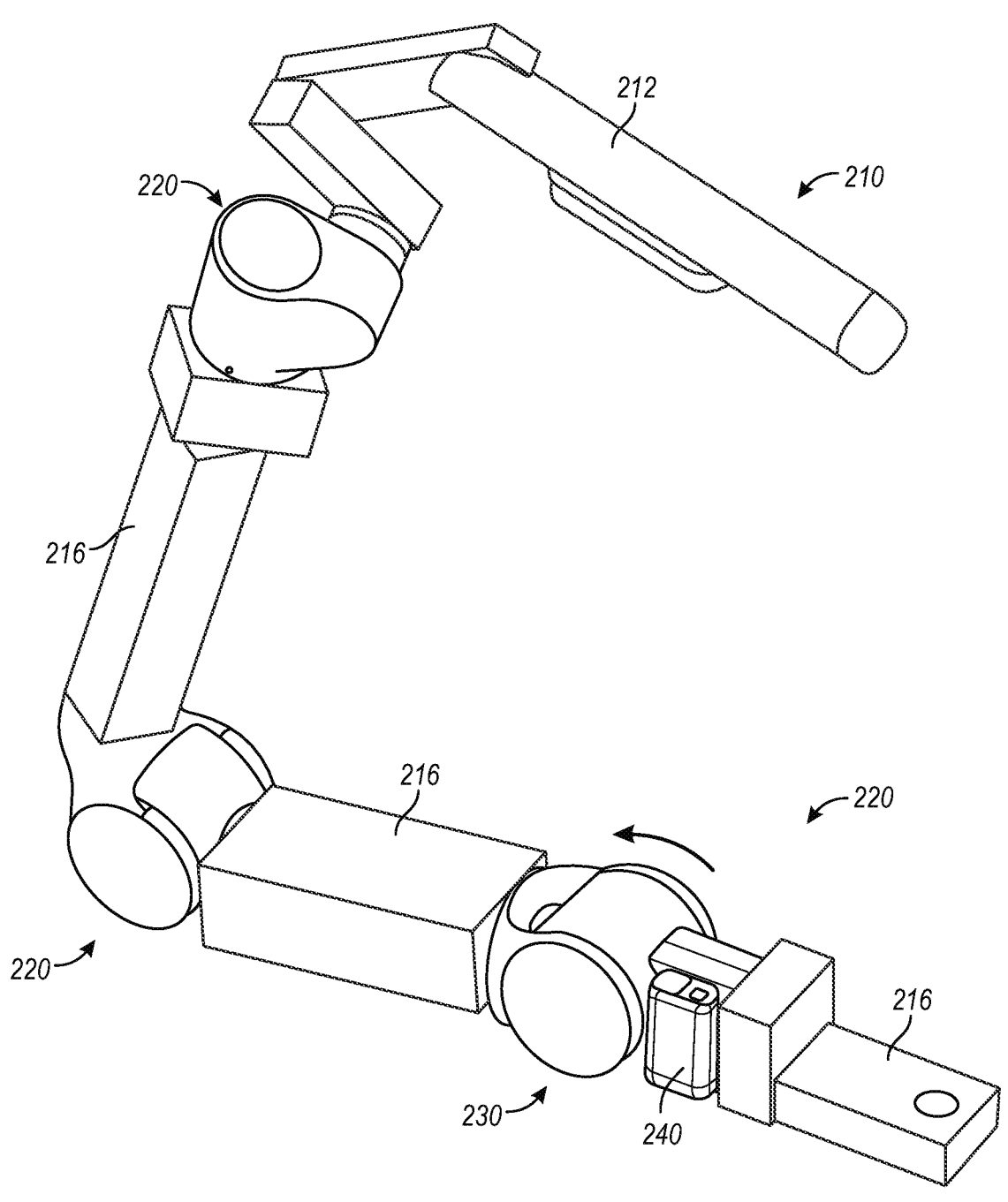
FIG. 21B illustrates an arm of the system of FIG. 21A, in accordance with some embodiments.

Accordingly, FIGS. 21A and 21B illustrate a robotic system 200 which includes a plurality of movable joints 220 and links 216 to control movement of the instrument driver 212 and the instrument 214 to perform a surgical procedure. In addition to a primary brake release that may be available to release the power-off brake system, as discussed above, some embodiments of the robotic system 200 can further comprise a novel brake release system 230 with a secondary brake release mechanism or device 240 that can allow the user to release the power-off brake to permit the user to, for example, more easily manipulate the position of a robotic arm 210 while the robotic system 200 is in a power-off or faulted state. In some applications, the secondary brake release device 240 can be utilized in the event of a patient emergency or other clinically-relevant event that occurs at the same time as a robotic system fault, allowing the clinical operating team to move the arms 210 of the robotic system 200 to rapidly permit access to the patient. Further, in some applications, the brake release system 230 can be used with robotic systems that are configured to only permit a single arm to become immoveable under a fault, as well as robotic systems that are configured to permit multiple arms to become immovable under a fault. Optionally, the brake release system 230 can be used as a testing device to override a functioning control system to check the functionality of a braking system.

The brake mechanisms of the robotic system 200 can be associated and/or coupled to various joints 220 of the robotic system 200. In the depicted example, the joints 220 may be designed to resist manual force such that they cannot simply be overcome by manual force upon a power shut off or fault. In accordance with some embodiments disclosed herein, the robotic system 200 can comprise a brake release system 230 with a secondary brake release device 240 that can permit the user to override the brake mechanism associated with one or more of the joints 220. Advantageously, some embodiments of a brake release system 230 can allow a user to perform one of a variety of operations or procedures, including accessing a patient on the bed of the system or testing the functionality of the brakes, without impacting the connection between the power-off brake and the motor driver. In some applications, since the arms of the robotic system are not required to be back driven, the arms, joints, and brakes can be configured to be more robust and lock into place, offering increased integrity and function of the robotic system while providing flexibility to the user to selectively release brake mechanisms via brake release system 230 as required.

In some embodiments, the robotic system 200 can be configured such that the joints 220 comprise first and second portions or links 216 that are movable relative to each other and relative to the base 202. As illustrated, the second portion or link 216 can couple to a tool or instrument 214 via an instrument driver 212. The brake mechanism can selectively limit motion of the joint 220. The brake mechanism can have a braking material that is engageable between an engaged configuration and a disengaged configuration. In the engaged configuration, the braking material can limit a movement of the second portion or link 216 of the joint 220 relative to the first portion or link 216 of the joint 220, and in the disengaged configuration, the braking material can permit the movement of the second link 216 of the joint 220 relative to the first link 216 of the joint 220. The brake mechanism can also comprise an electromagnetic assembly that has a coil that can be energized to disengage the braking material from the engaged configuration to the disengaged configuration, thereby controlling a function of the brake mechanism. During operation, certain joints 220 may be selectively braked, while other joints 220 are allowed to remain active. In certain operations states (e.g. GCAB), brake mechanisms on all joints 220 can be disengaged, allowing all the joints 220 of the arm 210 to be repositioned.

Optionally, the joint 220 or other portions of the arm 210 can include additional resistive elements to provide nominal resistance to motion when the brake mechanism is disengaged. In some applications, nominal resistance can prevent the arm 210 from falling on the patient or otherwise moving in an unpredictable manner under the weight of the arm 210.

Further, in accordance with some embodiments disclosed herein, the robotic system 200 can also comprise a brake release system 230 with a user-commanded brake release device 240 that permits the user to disengage the braking mechanism independently of the primary control system. Thus, the user-commanded brake release device 240 can serve as an alternative means to releasing one or more of the brake mechanisms of the robotic system 200.

Figure 22:
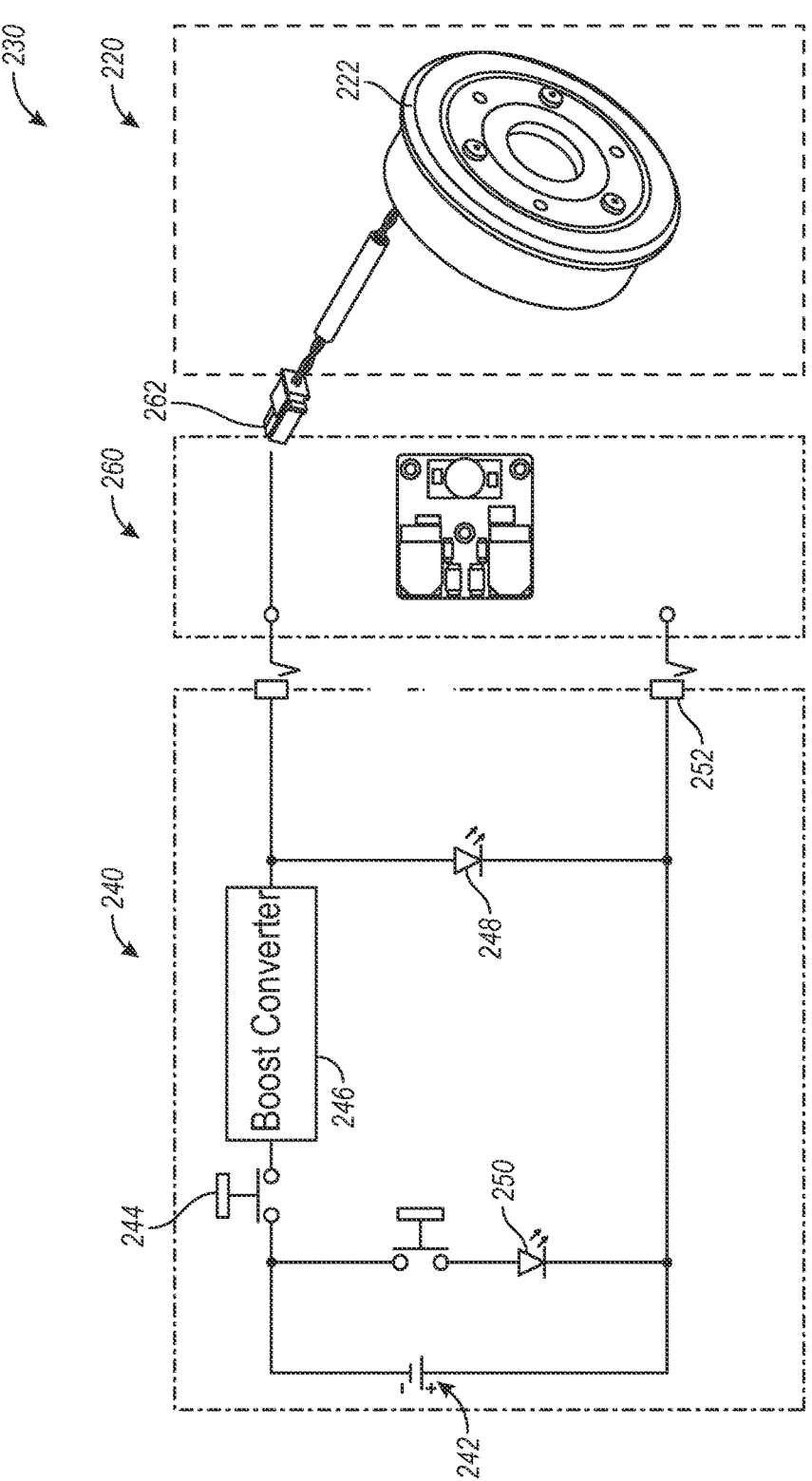
FIG. 22 depicts an electrical schematic diagram of a brake release device, in accordance with some embodiments.

FIG. 22 depicts an electrical schematic diagram of a brake release system 230, in accordance with some embodiments. As described herein, an electrical brake release system 230 can be used to selectively release a brake mechanism 222 associated with and/or coupled to one or more joints 220 or links 216 of a medical robotic system 200. Advantageously, embodiments of the brake release system 230 can provide a level of safety and ease-of-use for the user when desiring to move the arms 210 of the robotic system 200 during a power-off or fault state. In some embodiments, the brake release system 230 can release one or more joints 220 of a medical robotic system 200. Further, in some applications, the brake release system 230 can be utilized to release or otherwise control multiple joints 220 of a medical robotic system 200.

In the depicted example, the brake release system 230 can release a brake mechanism 222 independent of a control system of the robotic system 200 by bypassing the control system and applying appropriate current or power directly to the brake mechanism 222. In some embodiments, the brake release system 230 can apply an appropriate current or power to control or reduce the braking force of the brake mechanism 222 to allow user to move an arm 210, while providing nominal resistance to prevent the arm 210 from moving or falling due to its own weight.

In some embodiments, the brake release system 230 can utilize a brake release device with an independent power source, or any other suitable power source that is independent of the primary control system of the robotic system 200 to provide power to the brake mechanism 222.

As illustrated, the brake release device 240 can be electrically connected to the brake mechanism 222 to release or otherwise control operation of the brake mechanism 222. In some embodiments, one or more blade connectors 252 of the brake release device 240 can be connected to corresponding electrical connectors of a mounting plate 260. In some embodiments, the brake release device 240 can be electrically connected to the mounting plate 260 by other suitable connections, including, but not limited to contact connectors, such as pogo pins, or contactless connectors, such as an induction loop. The electrical connectors of the mounting plate 260 can be electrically connected to the brake mechanism 222 via an electrical connector 262. In some embodiments, the brake release device 240 can be directly electrically connected to the brake mechanism 222 without the interface of the mounting plate 260. In some embodiments, the mounting plate 260 and/or the brake release device 240 can be connected to multiple brake mechanism 222 corresponding to multiple joints 220 of a robotic system 200.

In the depicted example, the brake release device 240 is connected to the brake mechanism 222 using power and/or communication lines that are redundant to the lines between the primary control system and the brake mechanism 222. In some embodiments, the brake release device 240 and/or the mounting plate 260 is electrically connected to the brake mechanism 222 in parallel to the primary control system to allow the brake mechanism 222 to be released independently by either the primary control system or the brake release device 240. Optionally, the brake release device 240 and/or mounting plate 260 can be electrically connected to the brake mechanism 222 in any other manner that would allow the brake release device 240 to override or other wise provide a signal in lieu of the signal of the primary control system to release the brake mechanism 222.

In some embodiments, the brake release device 240 can be coupled to and/or carried by the robotic system 200. The brake release device 240 can be releasably or permanently coupled to components of the robotic system 200, such as the arm 210. For example, the body of the brake release device 240 can be coupled to the mounting plate 260. In some embodiments, the brake release device 240 can be integrated or otherwise incorporated into the robotic system 200, or components thereof.

In the depicted example, the brake release device 240 includes a power source or power supply 242 to energize the brake mechanism 222. In some embodiments, the power supply 242 can include one or more disposable batteries, rechargeable batteries, capacitors, power provided from a utility provider (i.e. grid power), and/or power directed from another portion or battery of the robotic system 200. In some embodiments, the power supply 242 can include a cord or connector to receive power from a utility provider or other source of power, independent of the control system. Optionally, the brake release device 240 and/or the brake release system 230 can include a charging circuit to charge the batteries or capacitor by energy received from the robotic system 200. In some embodiments, the batteries or capacitor can be charged by an external charging circuit. The external charging circuit can be integrated into the robotic system 200 or a standalone device. The brake release device 240 can include a dedicated port to connect the power supply 242 with the external charging circuit.

In some embodiments, the brake release device 240 can include a boost circuit or voltage regulator 246 to provide a desired output voltage range from the input received from the power supply 242. During operation, the voltage regulator 246 can increase the voltage level from the power supply 242 to a voltage suitable or otherwise capable for releasing the brake mechanism 222. In some applications, the brake mechanism 222 may require approximately 24 VDC within a tolerance range of +/−7% to disengage or release. Therefore, in some embodiments, the voltage regulator 246 may similarly be configured to provide approximately 24 VDC within the tolerance range of +/−7%. In some embodiments, the voltage regulator 246 can be disposed within the housing of the joint 220. Further, in certain applications, the power supply 242 may provide a voltage suitable for releasing the braking mechanism 222 without the use of a voltage regulator 246.

In the depicted example, a switch 244 can control the electrical connection between the power supply 242 and the brake mechanism 222, controlling the engagement and disengagement of the brake mechanism 222 by the brake release system 230. During operation, by engaging the switch 244, the operator can complete the circuit between the power supply 242 and the brake mechanism 222, providing sufficient voltage to release the brake mechanism 222 and permit movement of the respective joint 220. Upon disengaging the switch 244, the operator can break the circuit between the power supply 242 and the brake mechanism 222, permitting the brake mechanism 222 to return to a de-energized, engaged, or braked condition. In some embodiments, the switch 244 can be a momentary switch, a toggle switch, or any other suitable type of switch.

In some applications, operation of the brake release system 230 can be controlled from a remote location, such as a location outside the sterile field. For example, the switch 244 may be spaced apart from the body of the brake release device 240 and may be disposed within a physician console or tower. In some embodiments, operation of the switch 244 may be remotely controlled. Operation of the switch 244 may be remotely controlled from the physician console, tower, or other remote control device.

Further, in some applications, the brake release device 240 may not include a switch and may utilize the connection or disconnection of the brake release device 240 from the brake release system 230 to control the electrical connection between the power supply 242 and the brake mechanism 222, controlling the engagement and disengagement of the brake mechanism 222 by the brake release system 230. During operation, by connecting the brake release device 240 to the brake release system 230, the operator can complete the circuit between the power supply 242 and the brake mechanism 222, providing sufficient voltage to release the brake mechanism 222 and permit movement of the respective joint 220. Similarly, by disconnecting the brake release device 240 from the brake release system 230, the operator can break the circuit between the power supply 242 and the brake mechanism 222, permitting the brake mechanism 222 to return to a de-energized, engaged, or braked condition.

In some embodiments, the brake release system 230 generally can provide information regarding the overall status of the brake release system 230 and the status of the brake release device 240. For example, in some embodiments, the brake release system 230 can include a brake release indicator 248 to communicate the release state of the brake mechanism 222. During operation, the brake release indicator 248 can communicate if i) the brake mechanism 222 is engaged or braking the joint 220, ii) the brake mechanism 222 is disengaged or released. In some applications, the brake release indicator 248 can communicate if the brake mechanism is disengaged or released due to either the control system of the robotic system 200 or by the brake release system 230. In some applications, the brake release indicator 248 can include one or more lights (e.g. light emitting diodes), one or more audio signals, feedback that is communicated via a screen or graphical user interface, or feedback that is provided remotely via another device. In some embodiments, information regarding the brake release status can be communicated from the brake release system 230 to the robotic system 200 and may be displayed via a graphical user interface of the robotic system 200.

Further, in some embodiments, the brake release system 230 can include a battery status indicator 250 to communicate various parameters regarding a battery or power supply 242 of the brake release device 240. During operation, the battery status indicator 250 can communicate a battery voltage or state of charge, if a primary or secondary battery is currently in use, parameters regarding battery health, and current charging state. In some embodiments, battery status indicator 250 can initiate self-testing of the batteries or other suitable power supply 242. In some applications, the battery status indicator 250 can include one or more lights (e.g. light emitting diodes), one or more audio signals, feedback that is communicated via a screen or graphical user interface, or feedback that is provided remotely via another device. In some embodiments, the battery status indicator 250 may indicate the state of charge of the battery through a series of lights corresponding to a charge level. In some embodiments, information regarding the power supply 242 or battery status can be communicated from the brake release system 230 to the robotic system 200 and may be displayed via a graphical user interface of the robotic system 200. In some embodiments, status information and other parameters of the brake release system 230 may be displayed on a screen or other device via a graphical user interface. In some embodiments, a screen depicting a graphical user interface may be integrated into the brake release device 240.

In some embodiments, the brake release system 230 generally can include processing elements to sense and/or control operation of a robotic arm 210 or the robotic system 200 generally. For example, in some embodiments, during operation of the brake release device 240, the brake release system 230 can disconnect or otherwise disable power or communication lines from the primary control system of the robotic system 200, thereby overriding the robotic system 200. By disabling power or communication from the primary control system, the brake release system 230 can prevent an intentional brake disengagement initiated by the brake release system 230 from being inadvertently overridden by the primary control system.

In some embodiments, the brake release system 230 can detect or otherwise communicate with the robotic system 200 to determine if power has been lost or interrupted to the robotic system 200 and/or any specific joint 220. Further, in some applications, the brake release system 230 identify when the brake release system 230 should be utilized and inform/instruct the user to release a brake mechanism 222. Further, the brake release system 230 can communicate with the robotic system 200 to identify an unintentional brake disengagement initiated by the brake release system 230 and override the unintentional or accidental brake disengagement command.

In some embodiments, the brake release system 230 can perform a power on self test or other self-testing to identify any faults. Further, in some applications, additional information regarding the status of the brake release system 230, such as installation status of the brake release device 240, testing status of the brake release device 240, usage status of the brake release device system 230, etc. may be communicated from the brake release system 230 to the robotic system 200 and may be displayed via a graphical user interface of the robotic system 200.

In some applications, the brake release system 230 can including communication and/or data storage elements to record and/or convey information regarding the usage of the brake release system 230 or the interaction of the brake release system 230 with the robotic system 200 for retrieval or processing. For example, in some embodiments, the brake release system 230 may record operational information regarding the brake release system 230 in an event log. Optionally, the brake release system 230 can store information regarding the brake release system 230 within local memory. In some embodiments, information regarding the brake release system 230 can be stored within local memory of the brake release device 240. For example, the brake release system 230 may store and provide manufacturing information, previous usage information, operation logs of the arm or joint 220 associated with the brake release system 230, software version, etc.

During operation, components of the brake release device 240 can generate heat. In some embodiments, the brake release system 230 can include one or more components to control, regulate, or otherwise maintain a temperature of the brake release device 240. In some applications, the brake release system 230 can control, regulate, or otherwise maintain a casing or housing temperature of the brake release device 240 to permit a user to touch or otherwise handle the brake release device 240, in accordance with certain standards or specifications, such as IEC 60601-1.

Figure 23:
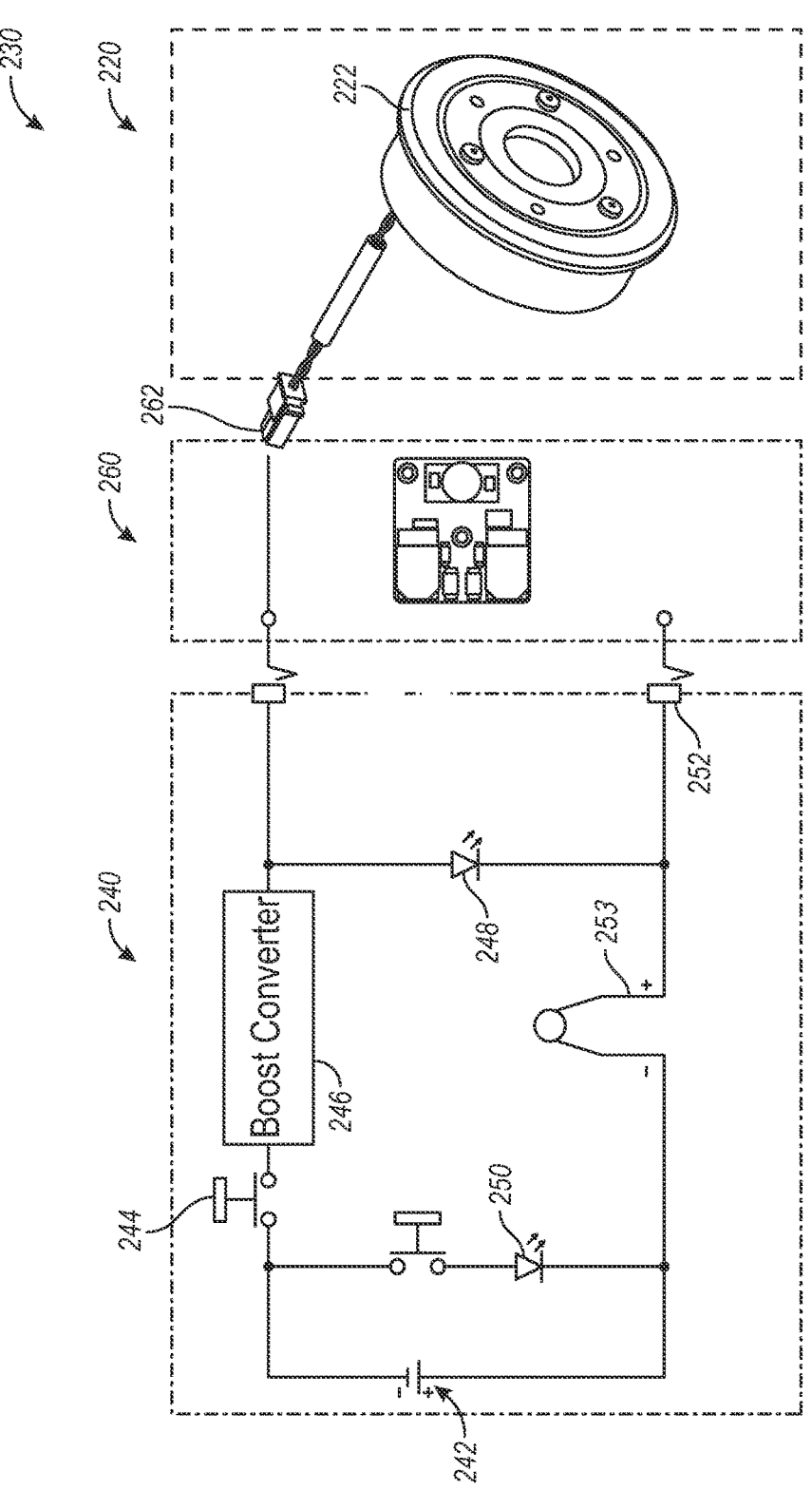
FIG. 23 depicts an electrical schematic diagram of a brake release device, in accordance with some embodiments.

FIG. 23 depicts an electrical schematic diagram of a brake release device 240, in accordance with some embodiments. In some embodiments, the brake release device 240 can include a thermocouple 253 to detect a temperature of one or more components of the brake release device 240 and allow the brake release system 230 control the temperature of the brake release device 240.

In the depicted example, the thermocouple 253 provides an output resistance in response to a detected temperature, which may correspond to a temperature of a component or housing of the brake release device 240. The thermocouple 253 can be connected to a circuit of the brake release system 230. In some applications, the output of the thermocouple 253 can be calibrated or characterized to correspond the resistance output of the thermocouple 253 with a measured temperature. Further, the temperature output of the thermocouple 253 can be calibrated or characterized to correspond to a casing or housing temperature, or otherwise the "touch" temperature that a user may experience when handling the brake release device 240.

In some embodiments, the brake release system 230 can adjust operation of the brake release device 240 in response to temperature feedback received from the thermocouple 253. For example, the brake release system 230 can reduce power directed to a brake release mechanism 222, reduce the amount of time the brake release system 230 is energized or otherwise in operation, and/or disable or shut down the brake release system 230 to reduce the temperature of the brake release device 240. In some embodiments, the feedback signal (e.g. resistance value) corresponding to the sensed temperature of the thermocouple 253 can be compared to a referenced value via a logic gate, such as an AND gate. The resulting signal can be provided to a microprocessor to reduce power or shut off power to portions of the brake release device 240.

Figure 24:
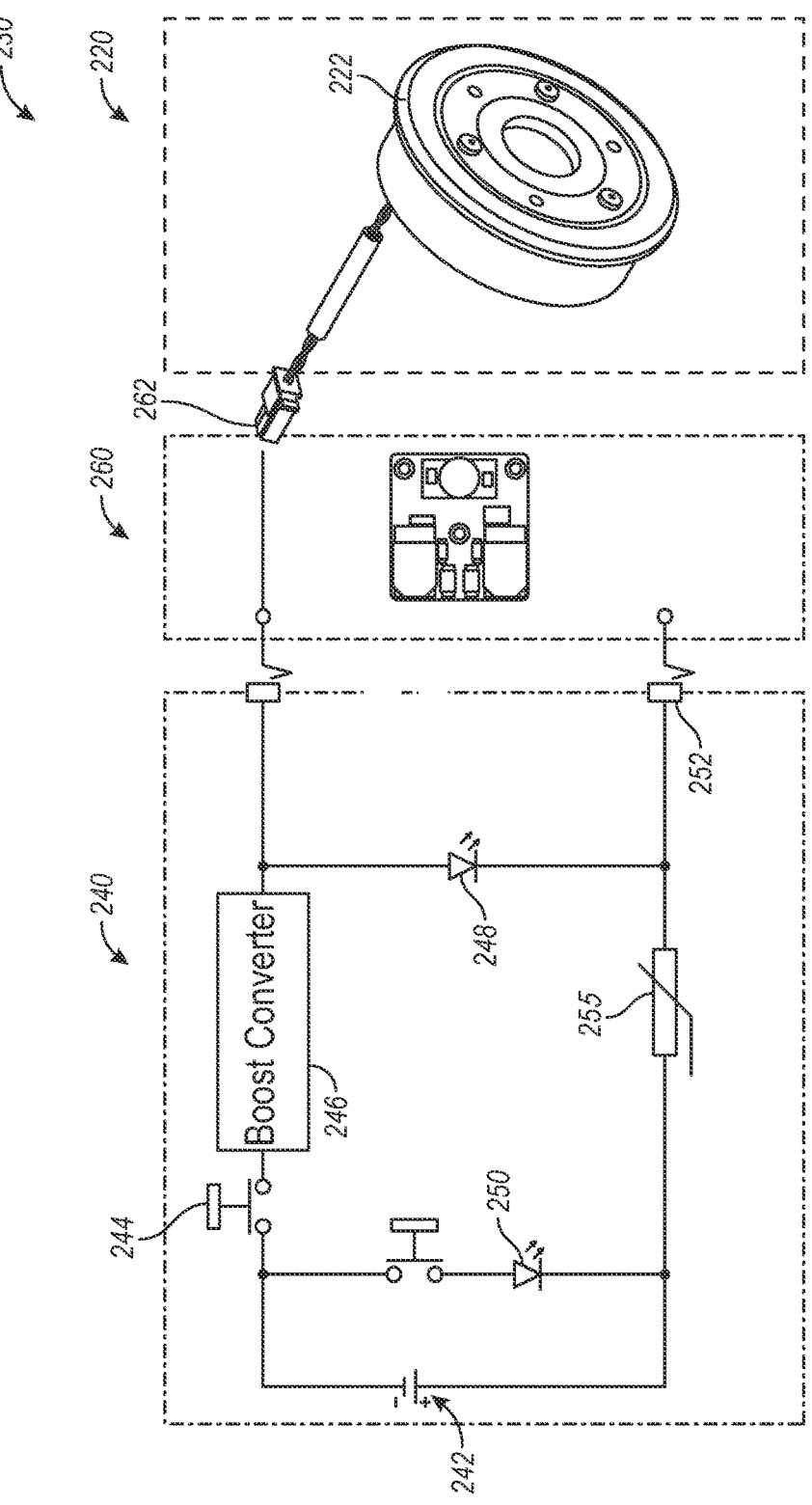
FIG. 24 depicts an electrical schematic diagram of a brake release device, in accordance with some embodiments.

FIG. 24 depicts an electrical schematic diagram of a brake release device 240, in accordance with some embodiments. In some embodiments, the brake release device 240 can include a thermistor 255 that allows the brake release system 230 control the temperature of the brake release device 240.

In the depicted example, the thermistor 255 can change or vary in resistance based on the temperature the thermistor 255 is exposed to. Therefore, the resistance of the thermistor 255 can correspond to an ambient temperature within the brake release device 240 or a component or housing of the brake release device 240. The thermistor 255 can be connected to a circuit of the brake release system 230. In some applications, the resistance of the thermistor 255 can be characterized to correspond with a measured temperature. Further, the resistance value of the thermistor 255 can be characterized to correspond to a casing or housing temperature, or otherwise the "touch" temperature that a user may experience when handling the brake release device 240.

In some embodiments, the brake release system 230 can adjust operation of the brake release device 240 in response to resistance values received from the thermistor 255. For example, the brake release system 230 can reduce power directed to a brake release mechanism 222, reduce the amount of time the brake release device 240 is energized or otherwise in operation, and/or disable or otherwise shut down the brake release system 230 to reduce the temperature of the brake release device 240. In some embodiments, the feedback signal (e.g. resistance value) corresponding to the sensed temperature of the thermistor 255 can be compared to a referenced value via a logic gate, such as an AND gate. The resulting signal can be provided to a microprocessor to reduce power or shut off power to portions of the brake release device 240.

In some embodiments, the thermistor 255 can be connected to an output of an amplification stage of the brake release device 240 such that the resistance value of the thermistor 255 can directly affect the output of the brake release device 240. During operation, as the resistance of the thermistor 255 varies with respect to temperature, the thermistor 255 can increase or decrease resistance experienced by the amplification stage of the brake release device 240, decreasing or increasing (respectively) the output power directed to the brake release mechanism 222 and controlling the heat output of the brake release device 240.

Figure 25:
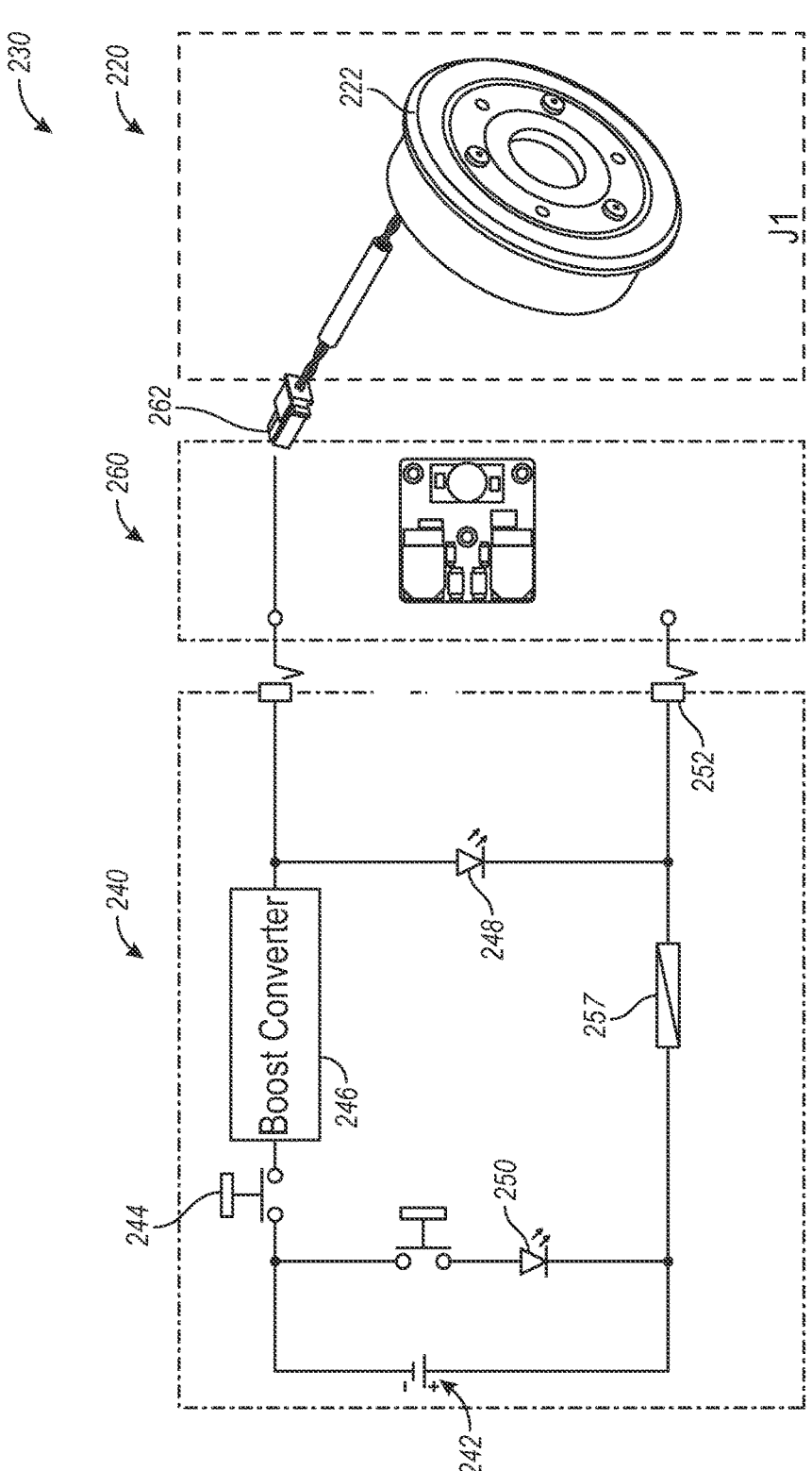
FIG. 25 depicts an electrical schematic diagram of a brake release device, in accordance with some embodiments.

FIG. 25 depicts an electrical schematic diagram of a brake release device 240, in accordance with some embodiments. In some embodiments, the brake release device 240 can include a thermal fuse 257 to open or break an electrical circuit of the brake release system 230 to allow the brake release system 230 control the temperature of the brake release device 240.

In the depicted example, the thermal fuse 257 can open or break an electrical circuit in response to the thermal fuse 257 exceeding a target or threshold temperature. The thermal fuse 257 can be calibrated or configured to open or break at a desired temperature. In some embodiments, the thermal fuse 257 can be calibrated to open or break at a temperature that permits an acceptable "touch" temperature that a user may experience when handling the brake release device 240.

In some embodiments, the thermal fuse 257 can be connected along various portions of a circuit of the brake release device 240 and/or brake release system 230 to isolate or otherwise portions of the brake release system 230 if the thermal fuse 257 exceed a threshold temperature. For example, the thermal fuse 257 can be disposed at the power supply 242 or before the boost converter or voltage regulator 246. In some embodiments, the thermal fuse 257 can be disposed after the boost converter or voltage regulator 246, within the mounting plate 260, or in other locations within the brake release system 230 and/or the robotic system 200. In some embodiments, the thermal fuse 257 can disable a portion of a circuit that generates heat during operation. Further, in some applications, the thermal fuse 257 can allow power to flow through other portions of the circuit to permit the brake release system 230 to communicate with the robotic system 200 and/or the user via graphical user interface to indicate that the brake release system 230 has overheated and the brake release device 240 has been disabled.

In some embodiments, the thermal fuse 257 can be a resettable fuse or breaker, that can be rearmed or reset after the thermal condition has passed or is addressed without replacing the thermal fuse 257. In some embodiments, the thermal fuse 257 may automatically reset.

In some embodiments, the thermal fuse 257 may be a single use fuse that may be replaced after exceeding a threshold temperature. In some embodiments, a replacement thermal fuse 257 may break or open in response to elevated temperatures for an extended period of time, protecting the brake release system 230 from components that are left energized for an extended period of time. In some embodiments, a user may be reminded to replace the batteries or power supply 242 of the brake release device 240 during the replacement of the thermal fuse 257.

In some embodiments, the brake release device 240 and/or the brake release system 230 can include a timing circuit to detect and control the duration of operation of the brake control system 230 to allow the brake release system 230 control the temperature of the brake release device 240.

In the depicted example, the timing circuit can allow the brake release device 240 or the brake release system 230 to operate for a predetermined period of time, which may correspond to a period of time for the brake release device 240 to reach an expected temperature. In some applications, the timing circuit can be calibrated or characterized to correspond a maximum operation time with a maximum acceptable or threshold temperature. Further, the operation time of the timing circuit can be calibrated or characterized to correspond to a maximum acceptable a casing or housing temperature, or otherwise the "touch" temperature that a user may experience when handling the brake release device 240. In the some embodiments, the timing circuit can include an analog oscillator circuit, a microprocessor, or any other suitable circuit.

FIG. 26 illustrates a perspective view of a joint 220 with a brake release device 240, in accordance with some embodiments. As illustrated, the brake release device 240 can be releasably coupled to portions of the robotic system 200, including, but not limited to, portions of the robotic arm 210, such as the link 216, the joint 220, or to portions adjacent to the link 216 and/or the joint 220. In some embodiments, the brake release device 240 can be externally coupled to the joint 220. Optionally, the brake release device 240 can be disposed within the robotic system 200 or otherwise integrated with the robotic system 200. In some embodiments, the brake release system 230 can include multiple brake release devices 240 to control multiple respective joints 220. The brake release devices 240 can similarly be coupled to portions of a respective robotic arm 210, or otherwise adjacent to a respective link 216 and/or joint 220.

In some embodiments, the brake release device 240 can be coupled to the robotic system 200 underneath or prior to the attachment of a sterile drape. Optionally, the brake release device 240 can be sterilized and coupled to the robotic system 200 or the robotic arm 210 outside of or over the sterile drape or otherwise after the attachment of the sterile drape on the robotic arm 210 or robotic system 200 generally. Advantageously, by sterilizing the brake release device 240, the brake release device 240 can be installed without compromising sterility of the robotic system 200. In some embodiments, the brake release system 230 and/or the robotic system 200 can identify if the brake release device 240 is coupled to the robotic system 200 either under or over a sterile drape.

FIG. 27 is a front elevation view of the brake release device 240 of FIG. 26. FIG. 28 is a cross-sectional side of the brake release device 240 of FIG. 26. With respect to FIGS. 26 and 27, components of the brake release device 240 described herein can be disposed in a common housing. In some embodiments, the components of the brake release device 240 can be disposed within the housing such that the housing can be configured to have a compact size (e.g. size of a pack of playing cards or smaller). Optionally, the housing of the brake release device 240 can be generally in the shape of a rectangular prism or any other suitable shape. As illustrated, components of the brake release device 240, including, but not limited to a power supply 242, a switch 244, a voltage regulator 246, and/or one or more blade connectors 252 can be arranged within the housing of the brake release device 240. In the depicted example, the blade connectors 525 of the brake release device 240 can extend beyond, through, or otherwise outside the housing to allow the brake release device 240 to electrically connect or otherwise interact with the robotic system 200.

As described herein, the brake release device 240 can be releasably coupled or mounted to robotic system 200. For example, the brake release device 240 can be releasably coupled adjacent to a joint 220. As illustrated, the brake release device 240 can include a latch, extension, or feature 254 configured to engage with a mating interface of the robotic system 200 or joint 220 to allow the brake release device 240 to be releasably attached thereto.

Figure 29:
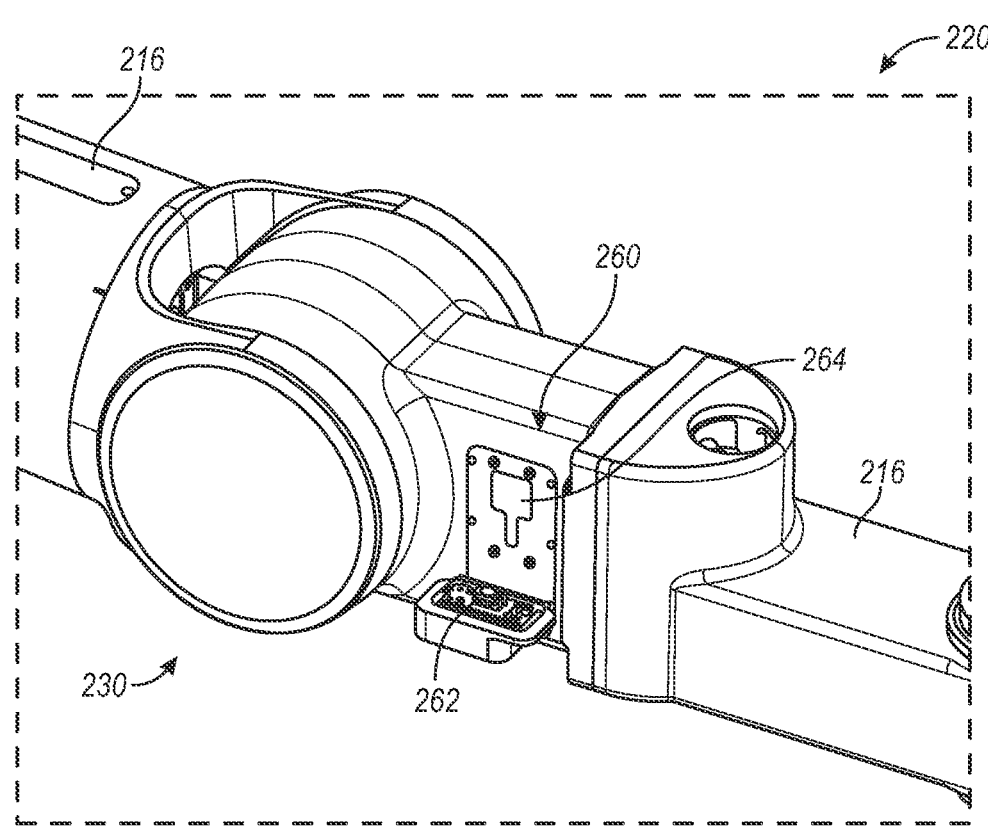
FIG. 29 illustrates a perspective view of the joint of FIG. 26.
Figure 30:
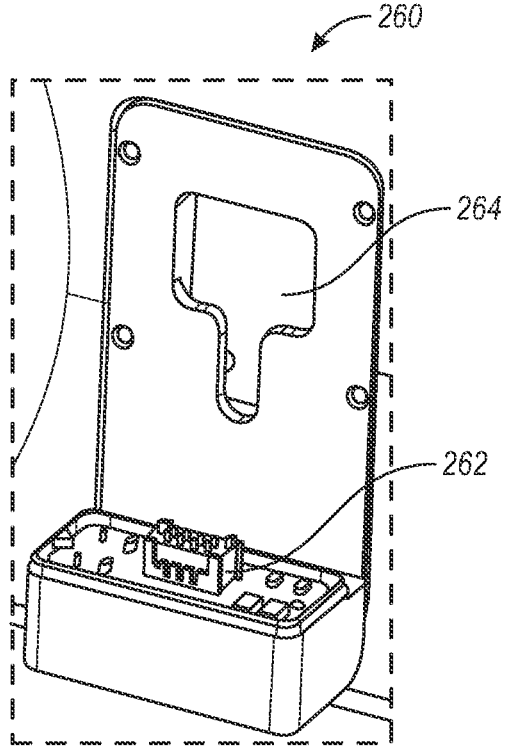
FIG. 30 illustrates a perspective view of a mounting plate, in accordance with some embodiments.

FIG. 29 illustrates a perspective view of the joint 220 of FIG. 26. FIG. 30 illustrates a perspective view of a mounting plate 260, in accordance with some embodiments. FIG. 31A illustrates a cross-sectional view of a brake release device 240 and the mounting plate 260 of FIG. 30, in accordance with some embodiments. FIG. 31B illustrates a cross-sectional view of a brake release device 240 and the mounting plate 260 of FIG. 30, in accordance with some embodiments. With reference to FIGS. 29-31B, the robotic system 200 can include an interface, attachment point, or mounting plate 260 to receive, releasably couple, or otherwise facilitate attachment of the brake release device 240 to the robotic system 200. As described herein, the mounting plate 260 can facilitate the physical attachment of the brake release device 240 to the robotic system 200 as well as facilitate the electrical connection, attachment, or interface between the brake release device 240 and the robotic system 200 (or a specific joint 220). As illustrated, the mounting plate 260 can be disposed on a portion of the robotic system 200, including, but not limited to on a link 216 or joint 220 of a robotic arm 210, or a portion of the robotic system 200 adjacent to a link 216 or joint 220.

In some embodiments, the mounting plate 260 includes or defines a slot 264 to engage with a portion of the brake release device 240 to releasably couple the brake release device 240 to the robotic system 200. As illustrated, the slot 264 of the mounting plate 260 can receive a portion or feature 254 of the brake release device 240 to releasably engage the brake release device 240 with the mounting plate 260. In some embodiments, the feature 254 can extend through the slot 264 to releasably capture a portion of the mounting plate 260 between the brake release device 240 housing and the feature 254. The slot 264 can include a wider portion or opening to facilitate location and insertion of the feature 254 within the slot 264 and a narrow portion to retain the feature 254 and brake release device 240 relative to the mounting plate 260. As illustrated, the feature 254 can be inserted and lowered within the slot 264 to retain the brake release device 240 within the mounting plate 260 and the feature 254 can be raised and removed through the slot 264 to remove the brake release device 240.

In some embodiments, the slot 264 can include a protrusion or feature to engage against a portion of the brake release device 240 to retain the brake release device 240 in an engaged position. In some embodiments, the mounting plate 260 can include a portion that extends outward to provide a travel stop for the brake release device 240 to locate or position the brake release device 240 relative to the mounting plate 260. Optionally, a portion of the electrical connector 262 of the mounting plate 260 can function as the travel stop for the brake release device 240.

In some applications, the mounting plate 260 may utilize other features or mechanisms to releasably couple with the brake release device 240. For example, the mounting plate 260 and the brake release device 240 may utilize a magnetic interface or clips to attach to the brake release device 240.

With reference to the schematic figures of FIGS. 22-25 (and the accompanying description) and illustrated in at least FIGS. 29-31B, the mounting plate 260 can further include an electrical connector 262 to facilitate an electrical connection between the brake release device 240 and the robotic system 200. As illustrated, the electrical connector 262 can engage with electrical connections of the brake release device 240, such as the blade connectors 252 of the brake release device 240, to allow for electrical signals to be passed between the brake release device 240 and the robotic system 200 to allow for the brake release device 240 to selectively release a brake mechanism of a joint 220. In some applications, the electrical connector 262 of the mounting plate 260 can be aligned or otherwise configured to permit an electrical connection between the brake release device 240 and the robotic system 200 when the brake release device 240 is mechanically engaged or retained by the mounting plate 260. In some embodiments, the electrical connector 262 can work in conjunction with the slot 264 to mechanically retain the brake release device 240. In some applications, the brake release device 240 can be electrically connected or in communication with the robotic system 200 without mechanically coupling the brake release device 240 to the mounting plate 260. In some embodiments, the brake release device 240 can be a handheld unit and wired or wirelessly connected to the robotic system 200. For example, in some applications, the electrical connector 262 can receive a connector from a handheld brake release device 240 spaced apart from the mounting plate 260.

In some embodiments, a clinician may install the brake release device 240 to the mounting plate 260 for an extended period of time or semi-permanently. In some applications, the brake release device 240 may be stored attached to the mounting plate 260 or removed and stored separate from the mounting plate 260. In some embodiments, the brake release device 240 can be stored under a surgical table, on a tower of the robotic system 200, or with any other portion or component of the robotic system 200. For example, the brake release device 240 can be stored on a designated shelf, or attached to a magnetized portion of the robotic system 200 (e.g. a magnetized portion of a base). In some embodiments, the brake release device 240 can be stored or attached to a hand-held element of the robotic system 200 to allow a clinician rapid access to the brake release device 240 if required.

In some embodiments, a storage location can include one or more sensors to detect the presence and status of the brake release device 240. For example, the robotic system 200 may inform a clinician if the brake release device 240 is stored, available, and/or ready for use. In some applications, the robotic system 200 may prevent or warn against the initiation of a procedure if the brake release device 240 is not available or ready for use. In some embodiments, the brake release device 240 can include an RFID or EEPROM component to communicate information regarding the device such as model, state of charge, last preventative maintenance, etc. to the robotic system 200. In some embodiments, the robotic system 200 may utilize hall sensors, reed switches, etc. to detect the presence or absence of the brake release device 240 from a storage location.

FIG. 32 illustrates a cross-sectional view of a brake release device 340 and a mounting plate 360, in accordance with some embodiments. In some embodiments, the brake release device 340 can include features and components similar to the features and components of the brake release device 240, including the features schematically depicted in at least in FIGS. 22-25 (and described in the accompanying description). With reference to FIG. 32, in some embodiments, the mounting plate 360 includes or defines a groove 364 to engage with a portion of the brake release device 340 to releasably couple the brake release device 340 to a robotic system. As illustrated, the groove 364 can receive a portion or feature 354 to releasably engage the brake release device 340 with the mounting plate 360. In some embodiments, a portion of the groove 364 and/or the feature 354 can deform or "snap" to retain the feature 354 within the groove 364 and retain the brake release device 340. During operation, a leading edge of the feature 354 can be inserted into the groove 364, allowing the feature 354 and the brake release device 340 to pivot relative to the mounting plate 360 and allowing the trailing edge of the feature 354 to engage, deform, or "snap" into place within the groove 364. Similarly, the feature 354 can be disengaged from the groove 364 to allow the brake release device 340 to be removed.

FIG. 33 illustrates a cross-sectional view of a brake release device 440 and a mounting plate 460, in accordance with some embodiments. In some embodiments, the brake release device 440 can include features and components similar to the features and components of the brake release device 240, including the features schematically depicted in at least in FIGS. 22-25 (and described in the accompanying description). With reference to FIG. 33, in some embodiments, the mounting plate 460 includes or defines sockets 464 to engage with one or more portions of the brake release device 440 to releasably couple the brake release device 440 to a robotic system. As illustrated, the sockets 464 can receive a prongs or extensions 454 to releasably engage the brake release device 440 with the mounting plate 460. In some embodiments, a portion of the sockets 464 and/or the extensions 454 can deform or "snap" to retain the extensions 454 within the sockets 464 and retain the brake release device 440. During operation, the extensions 454 can be inserted into the corresponding sockets 464, coupling the brake release device 440 to the mounting plate 460. Similarly, the extensions 454 can be pulled to be disengaged from the sockets 464 to allow the brake release device 440 to be removed.

Figure 34:
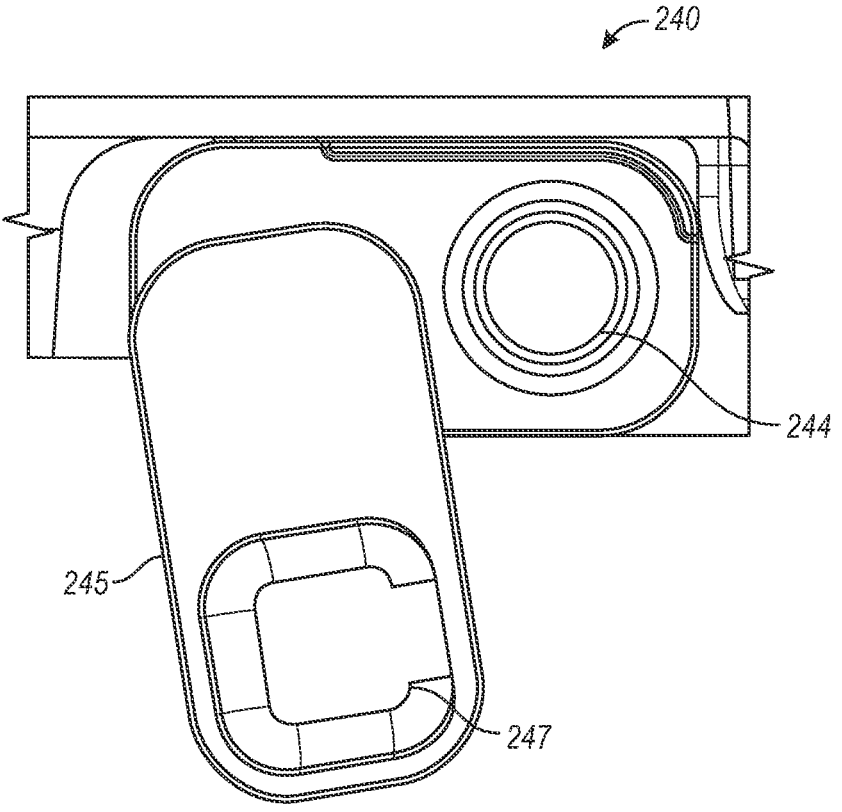
FIG. 34 illustrates a switch of a brake release device, in accordance with some embodiments.

FIG. 34 illustrates a switch 244 of a brake release device 240, in accordance with some embodiments. With reference to the schematic figures of FIGS. 22-25 (and the accompanying description) and illustrated in at least FIG. 34, the switch 244 allows a user to interface with or otherwise control the operation of the brake release device 240 and/or the brake release system 230. For example, the switch 244 can allow a user to selectively release a brake mechanism 222 to move a joint 220 using the brake release system 230. As described herein, the switch 244 can control the electrical connection of the power supply within the brake release device 240 and the brake mechanism of the joint 220.

In some embodiments, the switch 244 can be a push button disposed on an outer surface of the housing of the brake release device 240. As illustrated, the switch 244 can disposed on an upper surface of the housing of the brake release device 240. During operation, a user can depress or otherwise actuate the switch 244 to engage or disengage the switch 244 and therefore activate or deactivate the brake release device 240. In some embodiments, the switch 244 can be a momentary switch that requires the user to continuously press or actuate the switch 244 to activate the brake release device 240. In some embodiments, the switch 244 can be a latching switch that locks or engages in an activated or deactivated position, allowing the user to activate the brake release device 240 without continuously holding the switch 244. During operation, the switch 244 can be depressed, successively actuated, or otherwise moved to another position to deactivate the switch 244 and the brake release device 240. In some applications, the switch 244 can be recessed from a surface of the brake release device 240 housing to prevent a user from inadvertently activating the brake release device 240. Further, the actuation force and/or depth of the switch 244 can be configured to prevent inadvertent activation of the brake release device 240.

Figure 35:
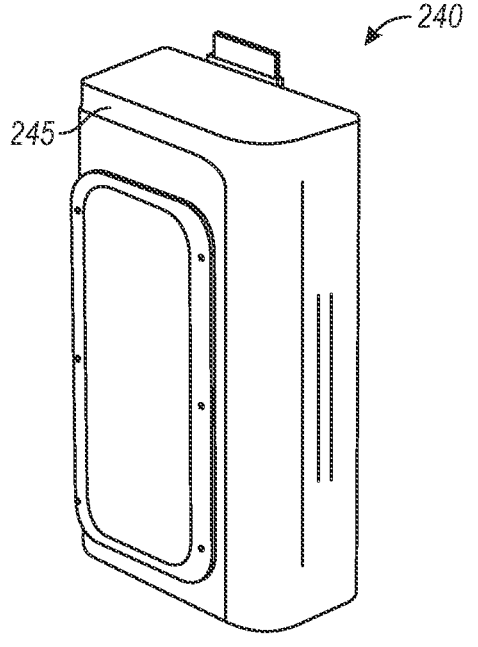
FIG. 35 illustrates a switch cover of the brake release device of FIG. 34, in accordance with some embodiments.

FIG. 35 illustrates a switch cover 245 of the brake release device of FIG. 34, in accordance with some embodiments. With reference to FIGS. 34 and 35, the brake release device 240 can include a switch cover 245 to limit inadvertent activation of the brake release device 240. As illustrated, the switch cover 245 can prevent accidental actuation of the switch 244 by obstructing or covering the switch 244 until the brake release device 240 intentionally activated. Prior to activation of the brake release device 240, the switch cover 245 can be moved or rotated to permit access to the switch 244. In some embodiments, the switch cover 245 includes an indentation 247 to facilitate movement or handling of the switch cover 245. Optionally, the switch cover 245 can be spring-loaded or biased to return to a closed or covered position. In some applications, when a clinician desires to release a brake mechanism of a robotic system a three-step process may be performed: in a first step, the brake release device 240 is installed on a mounting plate 260 of the robotic system 200, in a second step, a switch cover 245 is moved to permit access to the switch 244, confirming that the clinician intends to release the desired brake mechanism, and in a third step, the switch 244 is depressed, releasing the desired brake mechanism.

Figure 36:
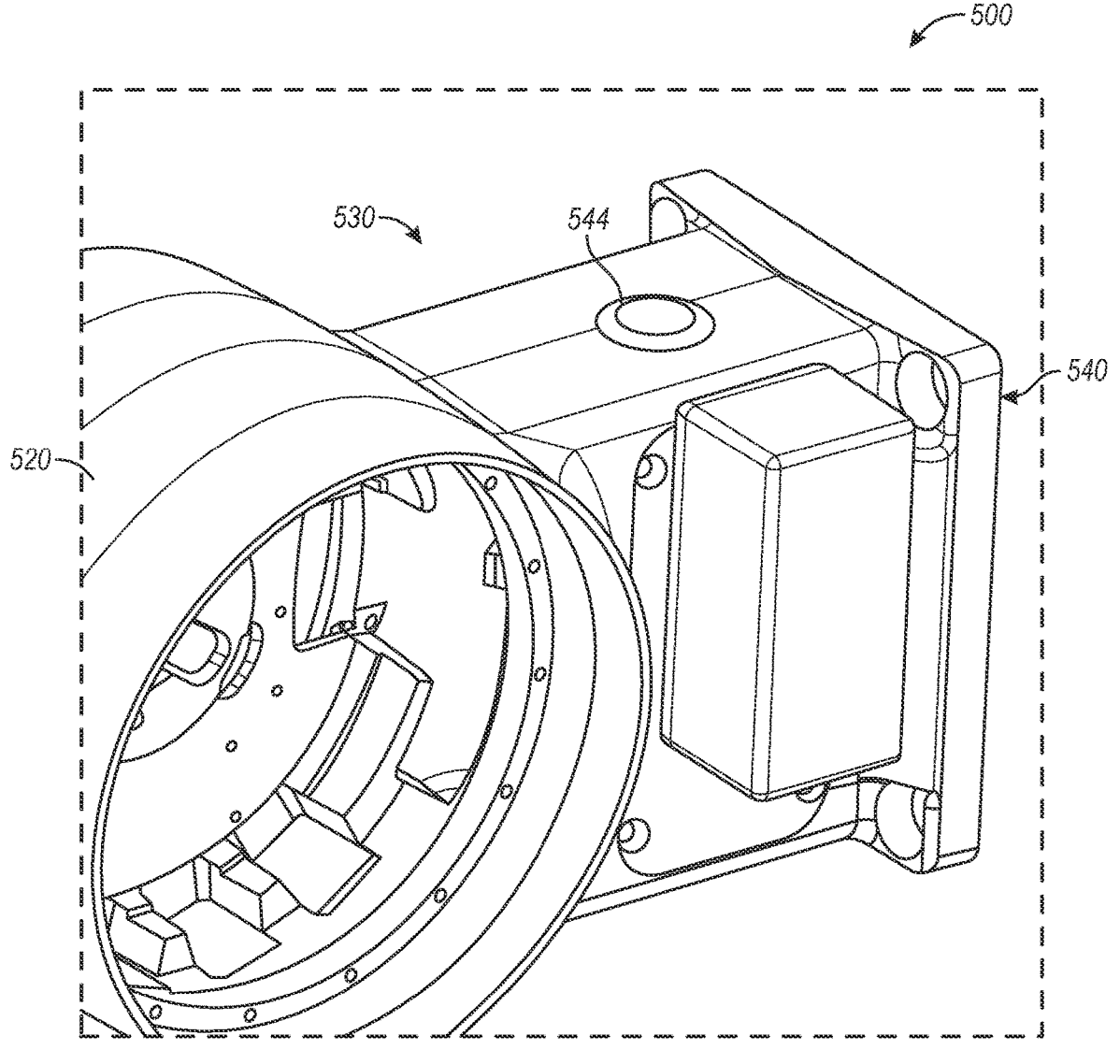
FIG. 36 illustrates a switch of a brake release device, in accordance with some embodiments.

FIG. 36 illustrates a switch 544 of a brake release device 540, in accordance with some embodiments. In some embodiments, the brake release device 540 can include features and components similar to the features and components of the brake release device 240, including the features schematically depicted in at least in FIGS. 22-25 (and described in the accompanying description). In some embodiments, the switch 544 can control operation of the brake release device 540 from a remote position spaced apart from the brake release device 540. As illustrated, the switch 544 can be independently disposed on any suitable portion or component of the robotic system 500. For example, the switch 544 can be disposed adjacent to a respective joint 520 of the robotic system 500. As described herein, the switch 544 can allow a user to selectively release a brake mechanism to move a joint 520 using the brake release system 530. Advantageously, by positioning the switch 544 remote or independent from the brake release device 540, the brake release device 540 can be disposed in any suitable location, while allowing the switch 544 to be disposed in a location accessible by the clinician. In some embodiments, the switch 544 can be positioned to avoid inadvertent activation of the brake release device 540.

Figure 37:
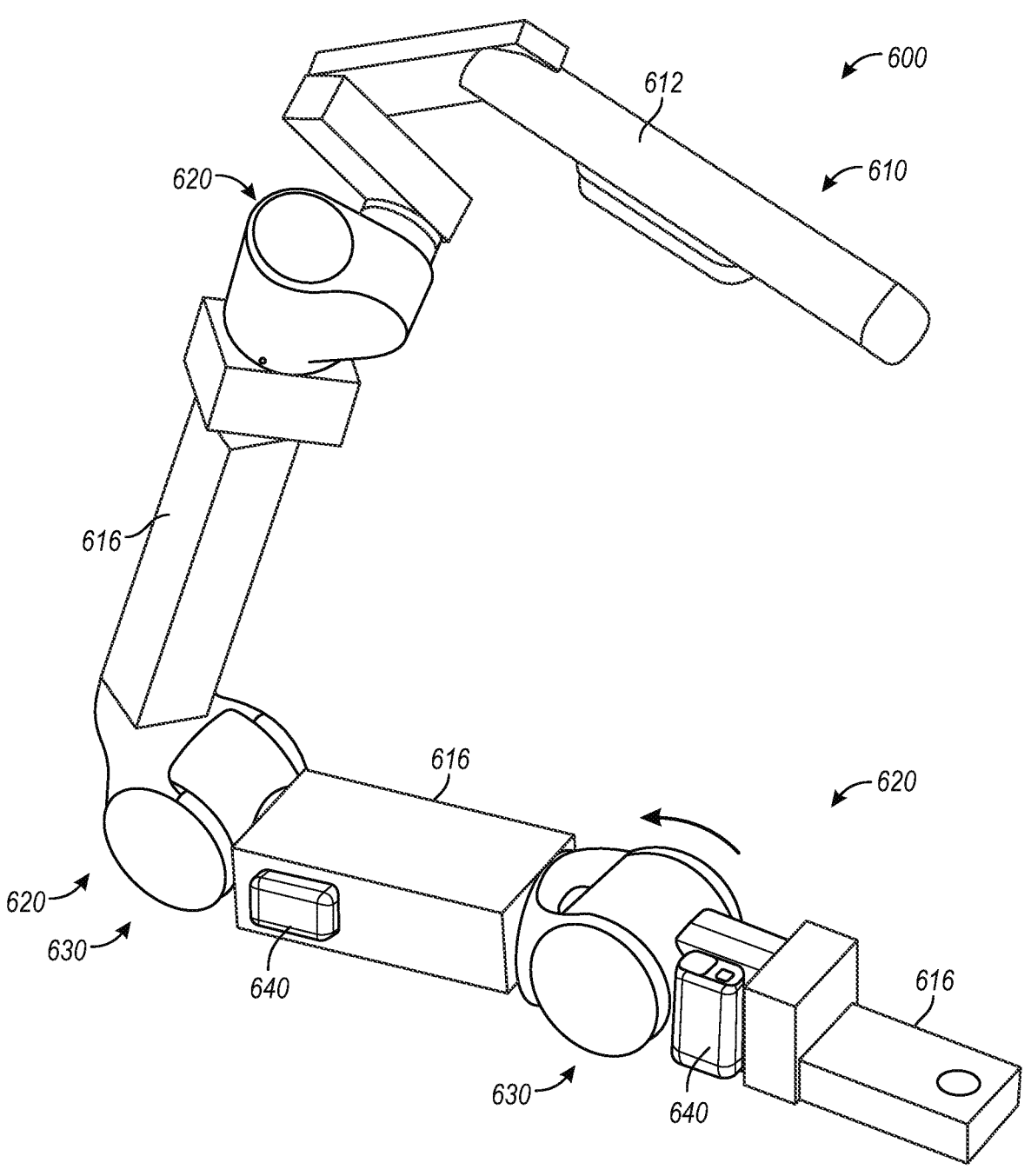
FIG. 37 illustrates a perspective view of an arm with multiple brake release devices, in accordance with some embodiments.

FIG. 37 illustrates a perspective view of an arm 610 with multiple brake release devices 640, in accordance with some embodiments. In some embodiments, the brake release devices 640 can each include features and components similar to the features and components of the brake release device 240, including the features schematically depicted in at least in FIGS. 22-25 (and described in the accompanying description). In the depicted example, the brake release system 630 can include multiple brake release devices 640 to control the operation of multiple respective joints 620. Accordingly, during operation, the brake release system 630 can allow a clinician to move multiple joints 620 of the arm 610 during a fault experienced by the robotic system 600 by utilizing multiple respective brake release devices 640. In some applications, a clinician may activate multiple brake release devices 640 in unison to simultaneously move multiple joints 620 of the arm 610. In some applications, a clinician may selectively or sequentially activate one or more brake release devices 640 to move one or more respective joints 620 at a time. As described herein, each brake release device 640 may correspond or otherwise interface with a respective joint 620. As illustrated, a brake release device 640 can be coupled or otherwise disposed adjacent to a respective joint 620 to be controlled by the brake release device 640. In some applications, a brake release device 640 may selectively control one or more joints 620 of the robotic system 600. Further, in some embodiments, a brake release device 640 may be moved between multiple positions or interfaces to interact with various respective joints 620 of the robotic system 600.

Figure 38:
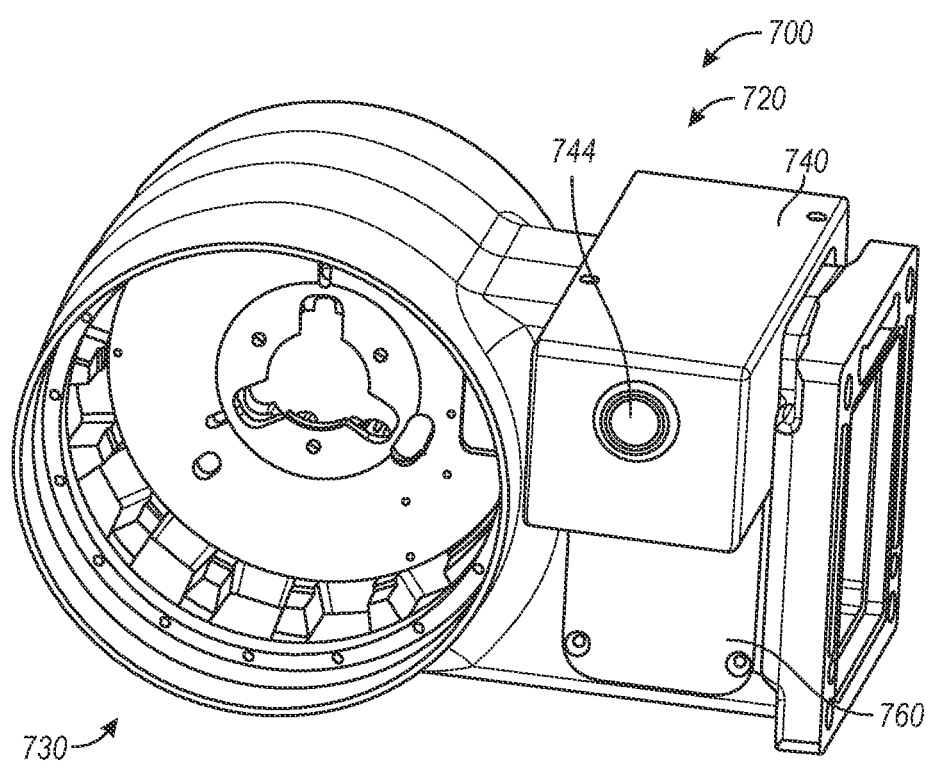
FIG. 38 illustrates a perspective view of a brake release device attached to an arm, in accordance with some embodiments.
Figure 39:
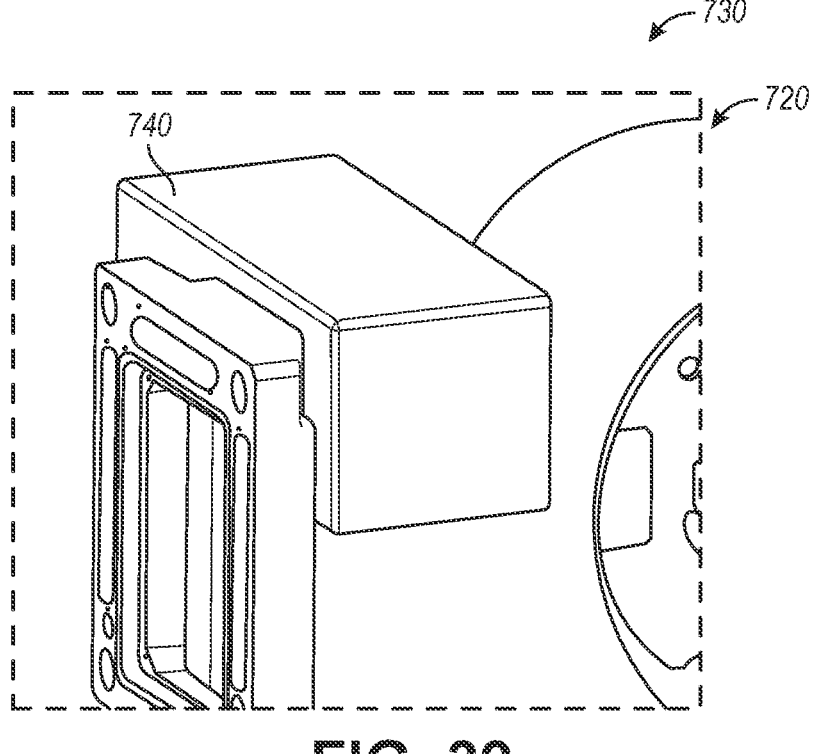
FIG. 39 illustrates a reverse perspective view of the brake release device of FIG. 38.
Figure 40:
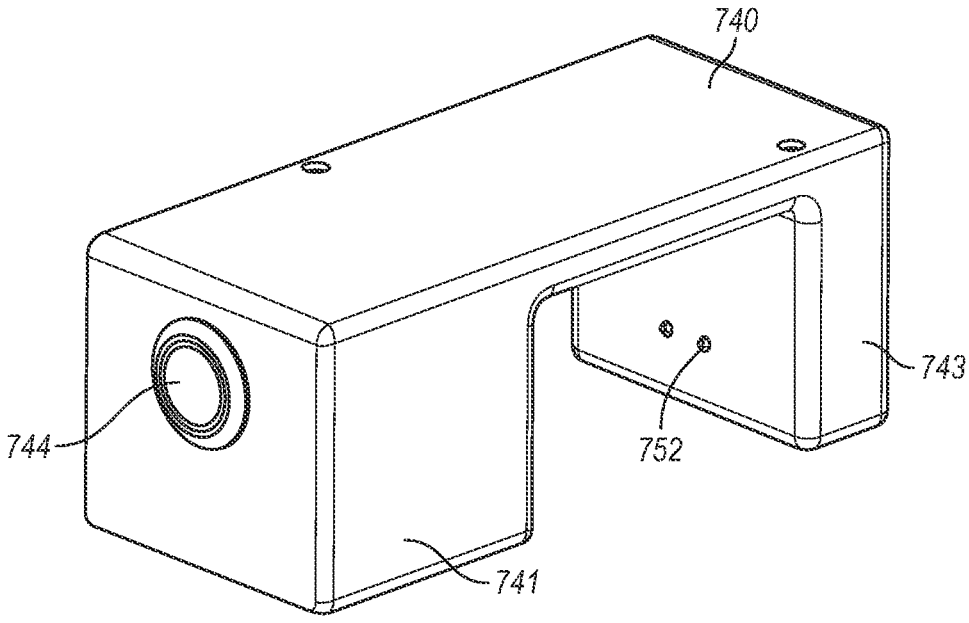
FIG. 40 is a perspective view of the brake release device of FIG. 38.
Figure 41:
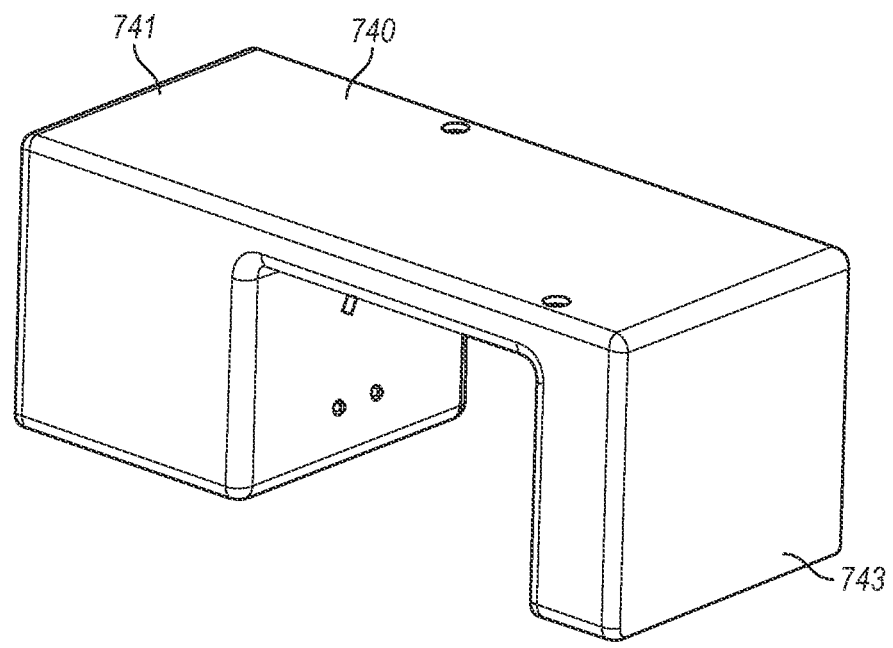
FIG. 41 is a reverse perspective view of the brake release device of FIG. 38.

FIG. 38 illustrates a perspective view of a brake release device 740 attached to an arm, in accordance with some embodiments. FIG. 39 illustrates a reverse perspective view of the brake release device 740 of FIG. 38. FIG. 40 is a perspective view of the brake release device 740 of FIG. 38. FIG. 41 is a reverse perspective view of the brake release device 740 of FIG. 38. In some embodiments, the brake release device 740 can include features and components similar to the features and components of the brake release device 240, including the features schematically depicted in at least in FIGS. 22-25 (and described in the accompanying description).

As illustrated, the brake release device 540 can be releasably coupled to portions of the robotic system 700, including, but not limited to, portions of the robotic arm, such as the link, the joint 720, or to portions adjacent to the link and/or the joint 720. In some embodiments, the brake release device 740 can be externally coupled to the joint 720.

In some embodiments, the housing of the brake release device 740 can be shaped or otherwise configured to fit around or rest on a portion of the robotic system 700. As illustrated, the housing of the brake release device 740 can be shaped to attach or rest to a top portion of joint 720 or a portion of the robotic system 700 adjacent to the joint 720. Advantageously, by forming or otherwise configuring the brake release device 740 to fit around a portion of the robotic system 700 an operator is not required to hold the brake release device 740 in place during operation. In some embodiments, the brake release device 740 can have a generally "U" or saddle shape.

As described herein, the brake release device 740 can be releasably coupled or mounted to robotic system 700. For example, the brake release device 740 can be releasably coupled adjacent to a joint 720. As illustrated, the brake release device 740 can include magnets or other features configured to engage with a mating interface of the robotic system 700 or joint 720 to allow the brake release device 740 to be releasably attached thereto.

Figure 42:
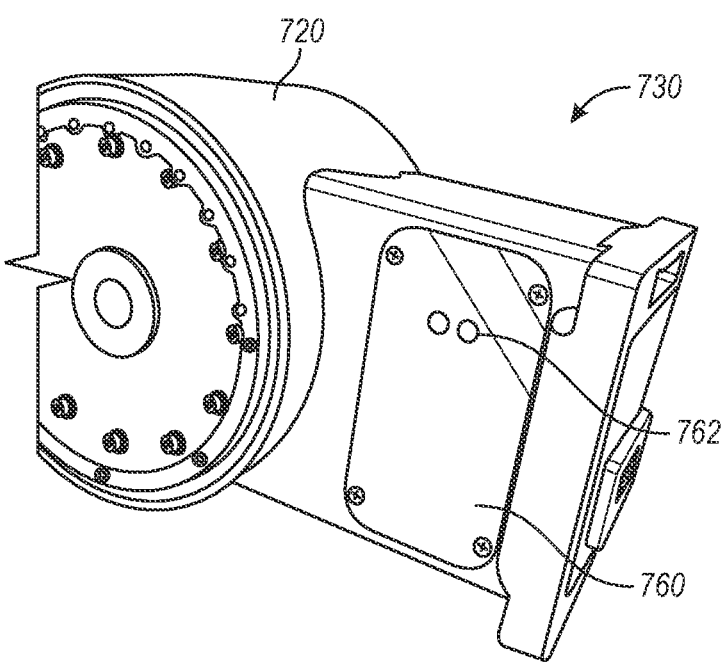
FIG. 42 is a perspective view of a mounting plate of the arm of FIG. 38, in accordance with some embodiments.

FIG. 42 is a perspective view of a mounting plate 760 of the arm of FIG. 38, in accordance with some embodiments. With reference to FIGS. 38-42, the robotic system 700 can include an interface, attachment point, or mounting plate 760 to receive, releasably couple, or otherwise facilitate attachment of the brake release device 740 to the robotic system 700. As described herein, the mounting plate 760 can facilitate the physical attachment of the brake release device 740 to the robotic system 700 as well as facilitate the electrical connection, attachment, or interface between the brake release device 740 and the robotic system 700 (or a specific joint 720). As illustrated, the mounting plate 760 can be disposed on a portion of the robotic system 700, including, but not limited to on a link or joint 720 of a robotic arm, or a portion of the robotic system 700 adjacent to a link or joint 720. In the depicted example, the mounting plate 760 can be positioned to allow the brake release device 740 to be placed around a portion of the robotic system 700.

In some embodiments, the mounting plate 760 includes one or more magnetic features engage with a portion of the brake release device 740 to releasably couple the brake release device 740 to the robotic system 700. In some embodiments, the mounting plate 760 includes multiple magnetic features, to align and releasably couple the brake release device 740 to the mounting plate 760. In some applications, the magnetic features can be the fasteners or other components of the mounting plate 760 that may also serve another purpose. As described herein, the brake release device 740 can include corresponding magnets to engage with the magnetic features of the mounting plate 760. Optionally, the mounting plate 760 can include magnets to engage with the brake release device 740. In some embodiments, the mounting plate 760 may include one or more detents, bumps, or other engagement features to provide additional engagement with the brake release device 740. The brake release device 740 can include corresponding features to engage with the engagement features of the mounting plate 760.

As illustrated, the mounting plate 760 can further include electrical contacts 762 to facilitate an electrical connection between the brake release device 740 and the robotic system 700. As illustrated, the electrical contacts 762 can engage with electrical connections of the brake release device 740. In the depicted example, the brake release device 740 includes pogo pins 752 configured to engage with the electrical contacts 762 to allow for electrical signals to be passed between the brake release device 740 and the robotic system 700. The pogo pins 752 can be spring-loaded or otherwise biased to ensure an electrical connection between the pogo pins 752 and the electrical contacts 762. In some applications, the electrical contacts 762 of the mounting plate 760 can be aligned or otherwise configured to permit an electrical connection between the brake release device 740 and the robotic system 700 when the brake release device 740 is mechanically engaged or retained by the mounting plate 760. In some applications, the brake release device 740 and the mounting plate 760 can utilize a wireless electrical connection, such as an inductive electrical connection.

Figure 43:
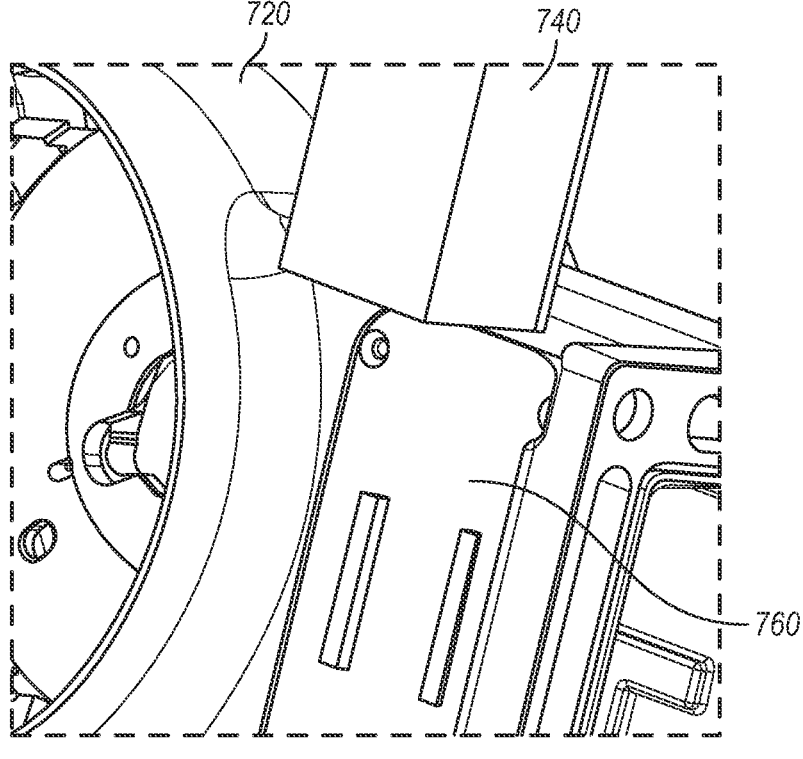
FIG. 43 is a perspective view of a mounting plate of the arm of FIG. 38, in accordance with some embodiments.

FIG. 43 is a perspective view of a mounting plate 760 of the arm of FIG. 38, in accordance with some embodiments. In some embodiments, the mounting plate 760 includes or defines one or more slots to engage with a portion of the brake release device 740 to releasably couple the brake release device 740 to the robotic system 700. During operation, the slots of the mounting plate 760 can receive a portion or indentation of the brake release device 740 to releasably engage the brake release device 740 with the mounting plate 760.

In some applications, the brake release device 740 may be stored attached to the mounting plate 760 or removed and stored separate from the mounting plate 760. In some embodiments, the brake release device 740 can be stored in a storage location away from the mounting plate 760. Optionally, the brake release device 740 can include one or more hinged portions to allow the brake release device 740 to lie flat during storage. Prior to operation, the brake release device 740 can be restored to a "U" or saddle shape. In some embodiments, the brake release device includes one or more ridges or detents to allow the brake release device 740 to "snap" into an operational configuration.

In some applications, functions and/or components of the brake release device, including the features schematically depicted in at least in FIGS. 22-25 (and described in the accompanying description), may be included in hand-held components of the robotic surgical system. For example, features and components of the brake release device may be included in a table remote or tower pendant of a robotic system.

3. Implementing Systems and Terminology

Implementations disclosed herein can advantageously provide systems, methods and apparatus for provide an added level of safety to a robot that interacts with humans, by allowing joints to be completely unlocked and repositioned even under complete electrical or software failure of the robot.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present inventions. Various modifications to these implementations will be readily apparent to those skilled in the art, and the generic principles defined herein may be applied to other implementations without departing from the scope of the inventions. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present inventions are not intended to be limited to the implementations shown herein but is to be accorded the widest scope consistent with the principles and novel features disclosed herein.

What is claimed is:

1. A release device configured to disengage an electromagnetic brake of a medical robotic system, the release device comprising:
    a release device body configured to removably couple to the medical robotic system;
    a switch positioned within the release device body;
    a power supply for providing power positioned within the release device body; and
    an electrical interface electrically connected to the power supply and configured to provide an electrical connection between the power supply and the electromagnetic brake when the release device body is coupled with the medical robotic system,
    wherein the electromagnetic brake is configured to be selectively energized by the power supply, independent of a control system of the medical robotic system, and in response to activation of the switch, to disengage the electromagnetic brake and permit articulation of a joint of a robotic arm of the medical robotic system.

2. The release device of claim 1, wherein the power supply comprises a battery carried by the body.

3. The release device of claim 2, further comprising a charging circuit electrically connected to the power supply and the electrical interface, wherein the charging circuit is configured to selectively charge the battery via the medical robotic system.

4. The release device of claim 1, wherein the power supply comprises a capacitor.

5. The release device of claim 1, further comprising a thermal protection circuit electrically connected to the power supply, wherein the thermal protection circuit is configured to reduce a power output of the release device in response to a device temperature exceeding a temperature threshold.

6. The release device of claim 5, wherein the thermal protection circuit comprises a thermistor or a thermocouple to detect the device temperature.

7. The release device of claim 5, wherein the thermal protection circuit comprises a thermal fuse to disable the power supply in response to the device temperature exceeding the temperature threshold.

8. The release device of claim 1, further comprising a timing circuit electrically connected to the power supply, wherein the timing circuit is configured to reduce a power output of the release device in response to a device operation period exceeding an operation period threshold.

9. The release device of claim 1, wherein the electrical interface comprises an inductive loop.

10. The release device of claim 1, wherein the release device is configured to communicate with the control system of the medical robotic system.

11. The release device of claim 1, the release device body being configured to removably couple with a mount on a robotic arm of the medical robotic system.

12. The release device of claim 1, the electrical interface including a plurality of electrical connectors, the plurality of electrical connectors being exposed relative to the release device body.

13. A method of operating a medical robotic system, the method comprising:

energizing a coil of an electromagnetic brake of a robotic joint of a robotic arm via power independent of a control system of the medical robotic system, the power being provided by a secondary power source, the secondary power source being contained within one or more of the following:

a body removably coupled with the medical robotic system, the body further including a switch coupled with the secondary power source, or the robotic arm;

disengaging the electromagnetic brake from the robotic joint in response to energizing the coil of the electromagnetic brake; and permitting articulation of the robotic joint in response to disengaging the electromagnetic brake from the robotic joint.

14. The method of claim 13, further comprising attaching a housing of the body to the medical robotic system.

15. The method of claim 12, further comprising actuating the switch to selectively energize the coil.

16. The method of claim 14, wherein a power source is carried by a housing of the robotic joint.

17. A medical robotic system comprising:

a robotic arm including a robotic joint, the robotic arm including a release device mount;

an electromagnetic brake assembly comprising:

a braking member engageable between an engaged configuration and a disengaged configuration, wherein in the engaged configuration the braking member limits an articulation of the robotic joint, and in the disengaged configuration the braking member permits the articulation of the robotic joint; and a coil coupled to the braking member, wherein the electromagnetic brake assembly is configured to disengage the braking member from the engaged configuration to the disengaged configuration when the coil is energized; and a release device comprising:

a power supply for providing power;

an interface electrically connected to the power supply and configured to provide an electrical connection between the power supply and the coil, wherein the coil is selectively energized by the power supply independent of a control system of the medical robotic system; and a body carrying the power supply and the interface, the body being configured to removably couple to the mount.

18. The medical robotic system of claim 17, wherein the robotic joint mount comprises a mounting plate configured to receive the body of the release device.

19. The medical robotic system of claim 16, further comprising:

a second electromagnetic brake assembly; and a second release device comprising:

a second power supply for providing power; and a second interface electrically connected to the power supply and configured to provide an electrical connection between the power supply and the second electromagnetic brake assembly, wherein the second electromagnetic brake assembly is selectively energized by the second power supply independent of the control system of the medical robotic system.

20. The medical robotic system of claim 17, the release device being configured to establish an electrical connection with the medical robotic system upon coupling of the body with the mount.

* * * * *